US012102369B2

United States Patent
Pedicini

(10) Patent No.: US 12,102,369 B2
(45) Date of Patent: Oct. 1, 2024

(54) SURGICAL IMPACTING TOOL INTERFACES

(71) Applicant: DePuy Synthes Products, Inc., Raynham, MA (US)

(72) Inventor: Christopher Pedicini, Franklin, TN (US)

(73) Assignee: DePuy Synthes Products, Inc., Raynham, MA (US)

( * ) Notice: Subject to any disclaimer, the term of this patent is extended or adjusted under 35 U.S.C. 154(b) by 441 days.

(21) Appl. No.: 17/319,700

(22) Filed: May 13, 2021

(65) Prior Publication Data

US 2022/0361934 A1    Nov. 17, 2022

(51) Int. Cl.
*A61B 17/92* (2006.01)
*A61B 17/16* (2006.01)
*A61B 17/00* (2006.01)

(52) U.S. Cl.
CPC .......... *A61B 17/92* (2013.01); *A61B 17/1604* (2013.01); *A61B 2017/00477* (2013.01)

(58) Field of Classification Search
CPC .............. A61B 17/162; A61B 17/1604; A61B 17/1659; B23B 31/101; B23B 31/103; B23B 31/107; B23B 31/1073; B23B 31/10741; B23B 31/1078; B23B 31/123; B23B 31/1261; B23B 31/16004; B23B 31/1612; Y10S 279/904; Y10T 403/65;

(Continued)

(56) References Cited

U.S. PATENT DOCUMENTS

| 646,489 | A | * | 4/1900 | Cook | .............. B23B 31/1071 |
| | | | | | 279/81 |
| 1,112,349 | A | * | 9/1914 | Barnes | .............. B23B 31/1078 |
| | | | | | 279/74 |

(Continued)

FOREIGN PATENT DOCUMENTS

| DE | 3714679 A1 | 11/1988 |
| EP | 2693957 B1 | 10/2016 |

OTHER PUBLICATIONS

International Search Report and Written Opinion for Intl. App. No. PCT/IB2022/054335 mailed Jul. 20, 2022.

(Continued)

*Primary Examiner* — David W Bates
(74) *Attorney, Agent, or Firm* — Mintz Levin Cohn Ferris Glovsky and Popeo, P.C.

(57) ABSTRACT

Various exemplary surgical impacting tool interfaces and methods of using surgical impacting tool interfaces are provided. In general, a surgical impacting tool includes a locking assembly configured to releasably attach to an adapter. In response to engagement with the adapter, the locking assembly is configured to move from an unlocked configuration, in which the adapter is not releasably attached to the surgical impacting tool (nor is any other adapter releasably attached to the surgical impacting tool via the locking assembly), to a locked configuration, in which the adapter is releasably attached to the surgical impacting tool via the locking assembly. The locking assembly is configured to receive the adapter in a longitudinal direction along a longitudinal axis defined by the locking assembly and to automatically lock the adapter to the surgical impacting tool.

20 Claims, 12 Drawing Sheets

(58) Field of Classification Search
CPC ..... Y10T 279/17076; Y10T 279/17136; Y10T 279/17153; Y10T 279/17162; Y10T 279/17179; Y10T 279/17213; Y10T 279/17239; Y10T 279/17256; Y10T 279/17367; Y10T 279/17487; Y10T 279/17572; Y10T 279/17581; Y10T 279/17589; Y10T 279/17692; Y10T 279/17717; Y10T 279/17743; Y10T 279/17769; Y10T 279/17803; Y10T 279/182; Y10T 279/1926; Y10T 279/906; F16B 2/06; F16B 2/10; F16B 2/12; F16B 37/0821; F16B 37/0864; F16B 37/0892; F16B 21/18; B25D 17/082; B25D 17/086; B25D 17/088; B25D 2217/0034; B25D 2217/0038; B25D 2217/0046; B25D 2217/0049; B25D 2217/0053

See application file for complete search history.

(56) References Cited

U.S. PATENT DOCUMENTS

| | | | | |
|---|---|---|---|---|
| 1,177,869 | A * | 4/1916 | Kelley | B23B 31/103 403/301 |
| 2,012,280 | A * | 8/1935 | Johansen | E21B 3/04 175/414 |
| 2,731,273 | A * | 1/1956 | Edens | B23B 31/113 279/81 |
| 2,827,316 | A * | 3/1958 | Duffy | F16B 2/10 403/366 |
| 2,886,355 | A * | 5/1959 | Wurzel | F16B 21/18 285/321 |
| 2,894,759 | A * | 7/1959 | De Bruin | B23B 31/107 279/97 |
| 3,030,121 | A * | 4/1962 | Scott | B23B 31/107 279/19.5 |
| 3,498,624 | A * | 3/1970 | Koch | B23B 31/10741 279/81 |
| 3,612,552 | A * | 10/1971 | Brundler | B23B 31/06 279/90 |
| 3,622,170 | A * | 11/1971 | Sedgwick | B23B 31/261 279/109 |
| 3,747,946 | A * | 7/1973 | Edens | B23B 31/10741 279/81 |
| 3,970,323 | A * | 7/1976 | Schnizler, Jr. | B23B 31/123 279/81 |
| 4,188,041 | A * | 2/1980 | Soderberg | B23B 31/22 279/81 |
| 4,552,136 | A * | 11/1985 | Kenna | A61B 17/1668 606/85 |
| 4,594,036 | A * | 6/1986 | Hogenhout | B23B 31/1215 279/74 |
| 4,626,146 | A | 12/1986 | Neumaier | |
| 4,663,999 | A * | 5/1987 | Colvin | B25B 13/18 279/74 |
| 4,716,794 | A * | 1/1988 | Leppanen | E21B 19/16 279/71 |
| 4,768,909 | A * | 9/1988 | Warkotsch | G01M 1/045 411/432 |
| 4,921,493 | A * | 5/1990 | Webb, Jr | A61B 17/1659 606/85 |
| 5,006,121 | A * | 4/1991 | Hafeli | A61B 17/1659 606/85 |
| 5,057,112 | A * | 10/1991 | Sherman | A61B 17/1659 606/86 R |
| 5,152,195 | A * | 10/1992 | Merrick | B25B 13/5075 81/53.2 |
| 5,315,902 | A * | 5/1994 | Ragland | B25B 13/5016 81/53.2 |
| 5,322,302 | A * | 6/1994 | Quirijnen | B23D 51/10 279/22 |
| 5,531,549 | A * | 7/1996 | Fossella | B25B 13/467 279/151 |
| 5,575,071 | A * | 11/1996 | Phillips | B23D 51/10 279/81 |
| 5,665,091 | A * | 9/1997 | Noble | A61B 17/1659 606/85 |
| 5,755,544 | A * | 5/1998 | Muller | F16B 37/0864 411/433 |
| 5,768,961 | A * | 6/1998 | Frawley | B25B 13/44 279/81 |
| 5,807,040 | A * | 9/1998 | Bongers-Ambrosius | B25D 17/088 408/239 R |
| 5,809,657 | A * | 9/1998 | Mortensen | B23D 49/11 30/392 |
| 6,120,508 | A * | 9/2000 | Grunig | A61B 17/1659 606/85 |
| 6,135,461 | A * | 10/2000 | Below | B25D 17/088 279/38 |
| 6,179,300 | B1 * | 1/2001 | Baumann | B23Q 3/12 279/82 |
| 6,209,208 | B1 * | 4/2001 | Marinkovich | B23D 51/10 271/81 |
| 6,467,379 | B1 * | 10/2002 | Wizman | B25B 13/102 81/185 |
| 6,550,786 | B2 * | 4/2003 | Gifford | B25B 23/0035 408/239 R |
| 6,735,876 | B2 * | 5/2004 | Hirabayashi | B23D 51/10 30/392 |
| 6,851,194 | B1 * | 2/2005 | Chen | B23D 51/10 30/392 |
| 7,062,996 | B2 * | 6/2006 | Johnson | B25B 13/44 81/157 |
| 7,264,429 | B2 * | 9/2007 | Miller | B23B 31/202 279/42 |
| 8,011,444 | B2 * | 9/2011 | Pyles | B23Q 5/20 173/171 |
| 8,393,409 | B2 | 3/2013 | Pedicini | |
| 8,695,726 | B2 | 4/2014 | Pedicini | |
| 8,893,592 | B2 * | 11/2014 | Womack | B25B 13/20 81/128 |
| 8,936,105 | B2 | 1/2015 | Pedicini | |
| 9,339,824 | B2 * | 5/2016 | Henne | B04B 9/00 |
| 11,170,745 | B1 * | 11/2021 | Cabo | F16B 2/10 |
| 11,300,151 | B2 * | 4/2022 | Bradshaw | F16B 37/0892 |
| 2002/0020974 | A1 * | 2/2002 | Wu | B23B 31/103 279/907 |
| 2002/0067008 | A1 * | 6/2002 | Frenzel | B25D 17/088 279/74 |
| 2002/0159830 | A1 * | 10/2002 | Fries | B23H 9/003 403/374.4 |
| 2003/0116334 | A1 * | 6/2003 | Funfer | B25D 11/005 173/132 |
| 2004/0084854 | A1 | 5/2004 | Hahn | |
| 2005/0199117 | A1 * | 9/2005 | Quinn | B23D 51/10 83/698.11 |
| 2005/0285355 | A1 * | 12/2005 | Lin | B23B 31/1071 279/81 |
| 2006/0022416 | A1 * | 2/2006 | Chen | B23B 31/107 279/74 |
| 2006/0083582 | A1 * | 4/2006 | Balsells | F16B 21/18 403/325 |
| 2007/0120331 | A1 * | 5/2007 | Manschitz | B23Q 3/12 279/19 |
| 2007/0235950 | A1 * | 10/2007 | Biedermann | B25D 17/088 279/19 |
| 2009/0051128 | A1 * | 2/2009 | Ghezzi | B23B 31/1269 279/74 |
| 2009/0200759 | A1 * | 8/2009 | Briggs | B23B 31/103 408/1 BD |
| 2009/0218452 | A1 * | 9/2009 | Kosiankowski | F16B 37/0842 248/74.1 |
| 2009/0252567 | A1 * | 10/2009 | Gillissen | B23 51/0473 408/239 R |
| 2009/0326540 | A1 * | 12/2009 | Estes | B23B 31/10741 279/78 |
| 2010/0000100 | A1 * | 1/2010 | Saegesser | B23D 51/10 30/337 |

(56) References Cited

U.S. PATENT DOCUMENTS

| | | | |
|---|---|---|---|
| 2011/0085876 A1* | 4/2011 | Wagner | F16B 37/0821 |
| | | | 411/433 |
| 2012/0148353 A1* | 6/2012 | Guy | B23B 31/1072 |
| | | | 407/108 |
| 2012/0299254 A1* | 11/2012 | Wanstrath | B25F 3/00 |
| | | | 279/143 |
| 2013/0161050 A1 | 6/2013 | Pedicini | |
| 2013/0204264 A1* | 8/2013 | Mani | A61F 2/4612 |
| | | | 623/22.11 |
| 2014/0276852 A1* | 9/2014 | Young | A61B 17/1668 |
| | | | 606/85 |
| 2016/0160900 A1* | 6/2016 | Milanowski | E04F 11/1817 |
| | | | 411/80.1 |
| 2017/0196710 A1* | 7/2017 | Behzadi | A61B 17/1659 |
| 2017/0340282 A1* | 11/2017 | Ferro | A61B 5/4571 |
| 2018/0055552 A1 | 3/2018 | Pedicini | |
| 2018/0055554 A1 | 3/2018 | Pedicini | |
| 2019/0183555 A1 | 6/2019 | Pedicini | |
| 2019/0293095 A1* | 9/2019 | Toyoda | B25B 11/02 |

OTHER PUBLICATIONS

International Preliminary Report on Patentability for Intl. App. No. PCT/IB2022/054335 mailed Nov. 23, 2023.
Medical Enterprises Distribution, Instructions For Use (IFU) ME1000 Adapters, dated Apr. 20, 2017. (60 pages).

\* cited by examiner

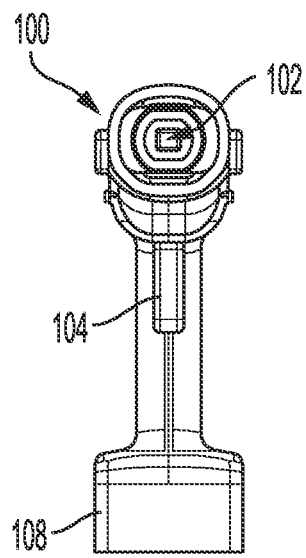 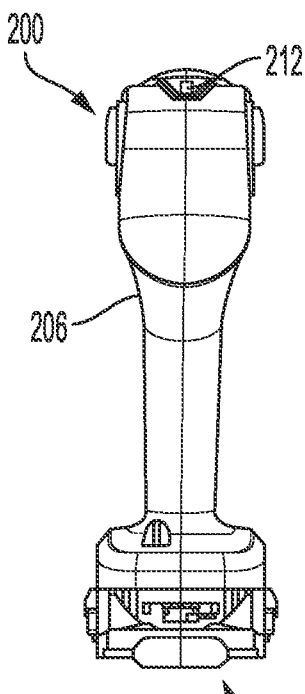 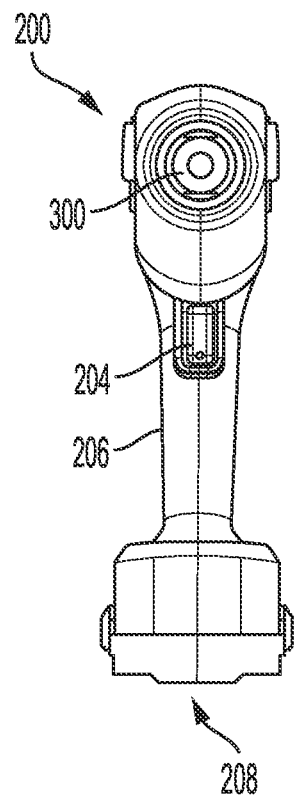
FIG. 3   FIG. 4   FIG. 5
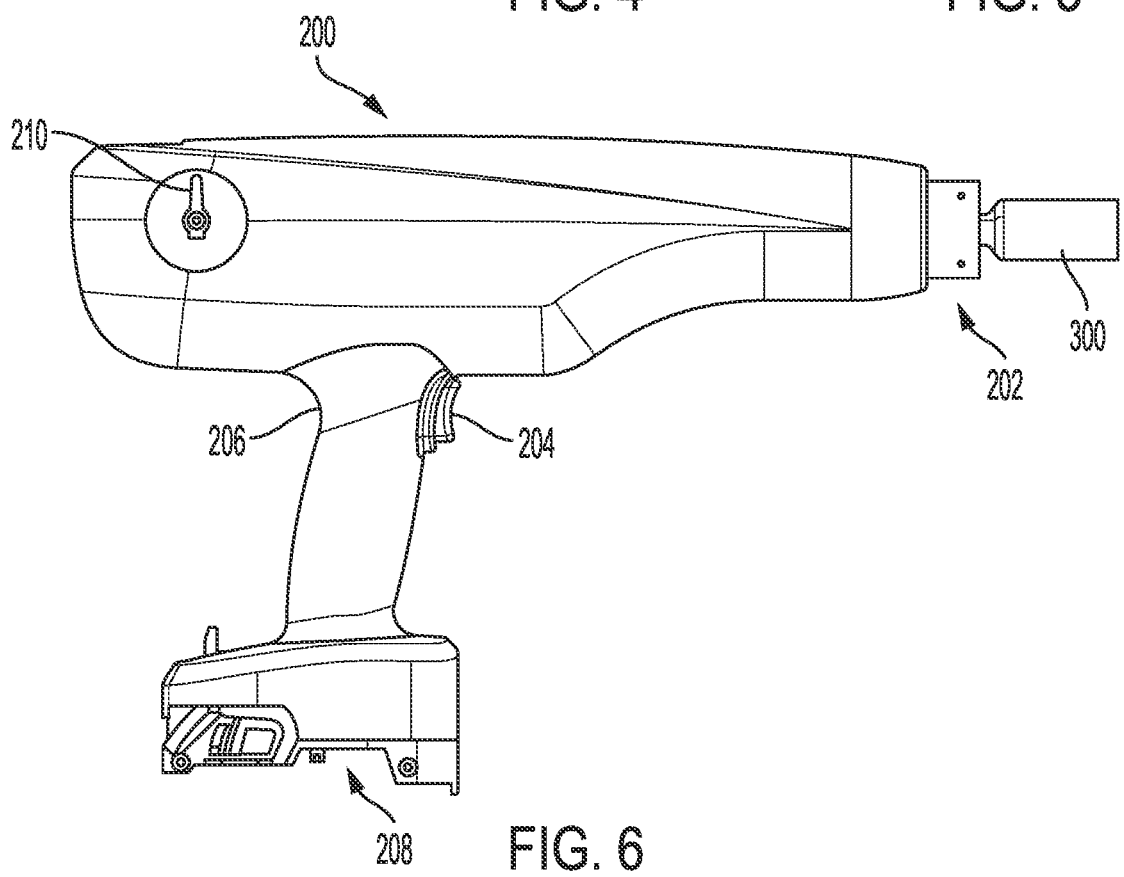
FIG. 6

SURGICAL IMPACTING TOOL INTERFACES

FIELD

The present disclosure relates generally to surgical impacting tool interfaces.

BACKGROUND

In the field of orthopedics, prosthetic devices, such as artificial joints, are often implanted or seated in a patient's bone cavity. The cavity is typically formed during surgery before a prosthetic device is seated or implanted by, for example, a physician or other medical professional removing and/or compacting existing bone to form the cavity. The prosthetic device, which can also be referred to as a prosthesis, usually includes a stem or other protrusion that is inserted into the cavity.

To create the cavity, a physician or other medical professional may use a broach, chisel, or other surgical implement conforming to the shape of the stem of the prosthetic device. In general, the surgical implement is impelled into the implant area to form the cavity. One technique for impelling the surgical implement includes a physician or other medical professional manual hammering the surgical impacting tool to impel the surgical implement into the implant area. Another technique for creating the prosthetic cavity relies on computer-controlled robotic arms for creating the cavity instead of using manual power provided by a physician or other medical professional. Another technique for creating the prosthetic cavity is to drive the surgical implement pneumatically, e.g., by compressed air. Another technique for creating the prosthetic cavity relies on a linear compressor to compress air on a single stroke basis and then, after a sufficient pressure is created, to release the air through a valve and onto a striker to impel the surgical implement.

The broach, chisel, or other surgical implement can be removably coupled to the surgical impacting tool to, for example, allow for surgical implements of different sizes and/or shapes to be used with the surgical impacting tool in different surgical procedures to help accommodate a particular patient's needs, to allow for replacement of surgical implements that become worn, damaged, or otherwise undesirable for future use without having to replace a remainder of the surgical impacting tool, and/or to accommodate a surgeon's personal preference of surgical implements. However, various techniques for creating the prosthetic cavity that impel the surgical implement, such as the four techniques discussed above, can loosen the surgical implement's removable coupling to the surgical impacting tool due to the force required to impel the surgical implement. Such loosening may cause the surgical implement to unexpectedly become decoupled from the surgical impacting tool during a surgical procedure, may cause the surgical implement to shake or otherwise move in unintentional direction(s) and thus cause patient harm and/or adversely affect cavity formation, and/or may hinder cavity formation by not allowing the surgical implement to receive and be impelled at full intended force.

Accordingly, there remains a need for improved surgical impacting tools.

SUMMARY

In general, surgical impacting tool interfaces and methods of using surgical impacting tool interfaces are provided.

In one aspect, a surgical tool is provided that in one embodiment includes an adapter configured to couple to a surgical implement configured to impact bone, and a locking assembly configured to releasably attach to the adapter. The locking assembly has a locked configuration in which the locking assembly is releasably attached to the adapter. The locking assembly has an unlocked configuration in which the locking assembly is not releasably attached to the adapter. The locking assembly includes a cavity configured to, in the locked configuration, seat a portion of the adapter therein. The locking assembly is configured to move from the unlocked configuration to the locked configuration in response to the adapter being moved into the cavity substantially along a longitudinal axis defined by the cavity and then rotating the adapter about the longitudinal axis. The locking assembly is configured to move from the locked configuration to the unlocked configuration in response to a housing of the locking assembly being rotated about the longitudinal axis and then the adapter being moved out of the cavity substantially along the longitudinal axis.

The surgical tool can have any number of variations. For example, the locking assembly can include a first pawl defining a first longitudinal axis that is substantially perpendicular to the longitudinal axis defined by the cavity with the locking assembly in the unlocked configuration, and a second pawl defining a second longitudinal axis that is substantially perpendicular to the longitudinal axis defined by the cavity with the locking assembly in the unlocked configuration.

For another example, the locking assembly can include a base having the cavity formed therein, a first pawl pivotally coupled to the base at a first pivot point, and a second pawl pivotally coupled to the base at a second pivot point. In some embodiments, the locking assembly can include a biasing element that biases the housing to a position corresponding to the unlocked configuration of the locking assembly. In some embodiments, the locking assembly being configured to move from the unlocked configuration to the locked configuration can include the adapter being moved into the cavity substantially along the longitudinal axis and thereby causing the first pawl to pivot at the first pivot point and the second pawl to pivot at the second pivot point. In some embodiments, the locking assembly being configured to move from the locked configuration to the unlocked configuration can include the housing being rotated about the longitudinal axis and thereby causing the housing to rotate relative to the base, and thereafter the adapter being moved out of the cavity substantially along the longitudinal axis and thereby causing the first pawl to pivot at the first pivot point and the second pawl to pivot at the second pivot point. In some embodiments, the locking assembly being configured to move from the locked configuration to the unlocked configuration can include the housing being rotated about the longitudinal axis and thereby causing the housing to rotate relative to the base, causing the first pawl to pivot at the first pivot point, and causing the second pawl to pivot at the second pivot point, and thereafter the adapter being moved out of the cavity substantially along the longitudinal axis. In some embodiments, the locking assembly can include a first biasing element that biases the housing to a position corresponding to the locked configuration of the locking assembly, and the locking assembly can include a second biasing element that biases the first and second pawls to positions corresponding to the locked configuration of the locking assembly.

For yet another example, the locking assembly can include a first pawl defining a first longitudinal axis that is substantially parallel to the longitudinal axis defined by the cavity with the locking assembly in the locked configuration, and a second pawl defining a second longitudinal axis that is substantially parallel to the longitudinal axis defined by the cavity with the locking assembly in the locked configuration.

For yet another example, the locking assembly can be configured to automatically move from the unlocked configuration to the locked configuration without the adapter being rotated.

For another example, the locking assembly can be configured to, in the locked configuration, seat the adapter in the cavity at each of a plurality of predetermined angular orientations relative to the locking assembly. In some embodiments, the plurality of predetermined angular orientations can each be about 90 degrees apart from one another.

For yet another example, the surgical tool can also include the surgical implement. In some embodiments, the surgical implement includes a chisel or a broach.

For another example, a surgical impacting tool can include the locking assembly; with the surgical implement operably coupled to the locking assembly, the surgical impacting tool can be configured to drive the impacting of the surgical implement; and a direction of the impacting can be substantially along the longitudinal axis defined by the cavity.

In another aspect, a surgical method is provided that in one embodiment includes releasably attaching an adapter to a locking assembly by moving the adapter into a cavity of the locking assembly substantially along a longitudinal axis defined by the cavity. The surgical method also includes driving impacting of a surgical implement relative to bone. The surgical implement is attached to the adapter, and a direction of the impacting is substantially along the longitudinal axis defined by the cavity.

The surgical method can vary in any number of ways. For example, the surgical method can also include detaching the adapter from the locking assembly by rotating a housing of the locking assembly about the longitudinal axis and then moving the adapter out of the cavity substantially along the longitudinal axis. For yet another example, the surgical implement can include a chisel or a broach. For still another example, the adapter can be releasably attached to the locking assembly without the adapter being rotated.

For another example, the locking assembly can include a housing, a first pawl, and a second pawl, and moving the adapter into the cavity can cause each of the first and second pawls to pivot relative to the housing. In some embodiments, the surgical method can also include, after moving the adapter into the cavity, rotating the housing about the longitudinal axis, thereby causing the first and second pawls to pivot relative to the housing and the adapter.

BRIEF DESCRIPTION OF DRAWINGS

The present invention is described by way of reference to the accompanying figures which are as follows:

FIG. 3 is a front view of the tool of FIG. 1;

FIG. 4 is a back view of another embodiment of a surgical impacting tool;

FIG. 5 is a front view of the tool of FIG. 4 with one embodiment of an adapter releasably attached thereto;

FIG. 6 is a side view of the tool and adapter of FIG. 5;

DETAILED DESCRIPTION

Figure 1:
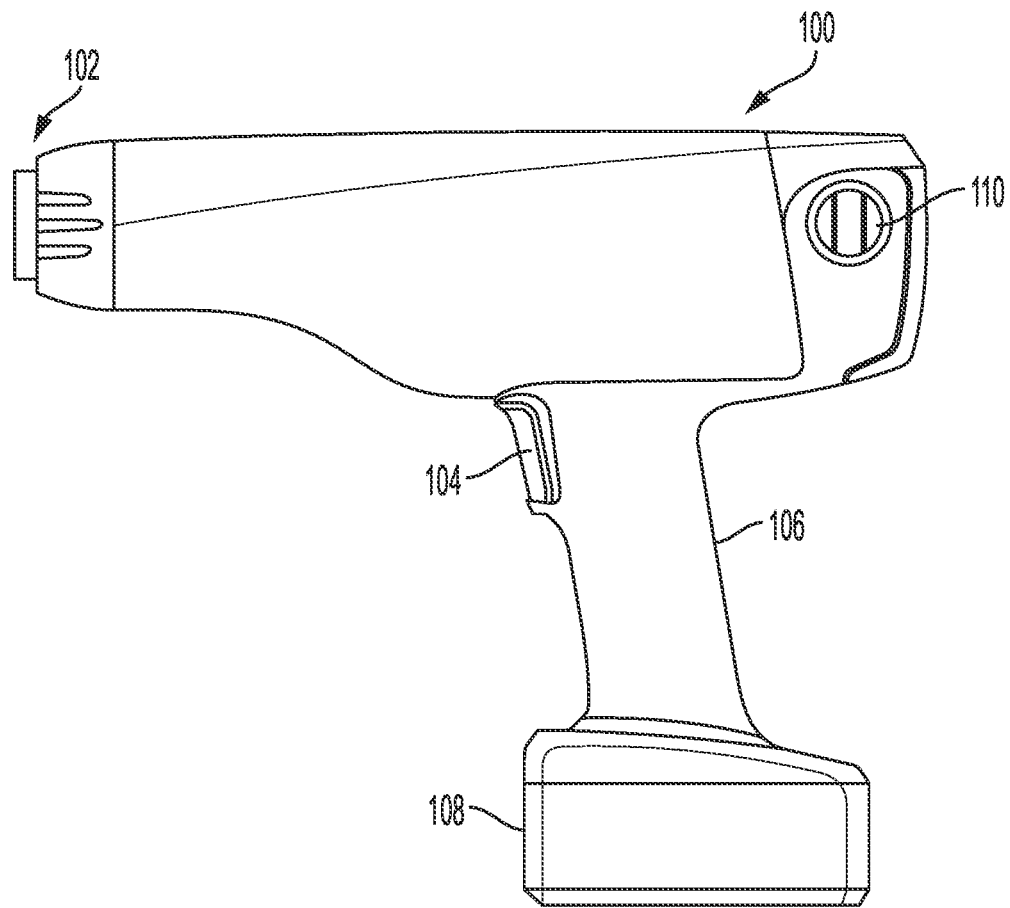
FIG. 1 is a side view of an embodiment of a surgical impacting tool.

Certain exemplary embodiments will now be described to provide an overall understanding of the principles of the structure, function, manufacture, and use of the devices, systems, and methods disclosed herein. One or more examples of these embodiments are illustrated in the accompanying drawings. A person skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the size and shape of components with which the systems and devices will be used.

Various exemplary surgical impacting tool interfaces and methods of using surgical impacting tool interfaces are provided. In general, a surgical impacting tool includes a locking assembly configured to releasably attach to an adapter. In response to engagement with the adapter, the locking assembly is configured to move from an unlocked configuration, in which the adapter is not releasably attached to the surgical impacting tool (nor is any other adapter releasably attached to the surgical impacting tool via the locking assembly), to a locked configuration, in which the adapter is releasably attached to the surgical impacting tool via the locking assembly. The locking assembly is configured to receive the adapter in a longitudinal direction along a longitudinal axis defined by the locking assembly and to automatically lock the adapter to the surgical impacting tool. In this way, the locking assembly may allow for quick and automatic attachment of the surgical impacting tool to the adapter. De-coupling of the adapter and surgical impacting tool may also be quickly and simply achieved by rotating the locking assembly relative to the adapter followed by longitudinal translation of the adapter relative to the locking assembly and the surgical impacting tool.

The adapter to which the surgical impacting tool is configured to attach is configured to releasably attach to a surgical implement configured to impact bone. The surgical impacting tool, such as an orthopedic impactor, is configured to drive impacting of the surgical implement relative to bone. The surgical impacting tool releasably attached to the adapter is configured to provide a force to the surgical implement, via the adapter, to drive the impacting of the surgical implement. Whether the force is a forward driving force for forward impacting or a rearward driving force for rearward impacting, the force is a longitudinal force along the longitudinal axis defined by the locking assembly. The locking assembly being configured to unlock from the adapter in response to rotational motion may thus help prevent the adapter (and a surgical implement attached thereto) from detaching from the surgical impacting tool during impacting since the longitudinally directed force from the surgical impacting tool will not urge rotational movement of the locking assembly.

The surgical implement configured to be attached to the adapter can be a broach, chisel, or other surgical implement. The surgical impacting tool being releasably attachable to the adapter allows the surgical impacting tool to be releasably attachable to a variety of different adapters, each of which can be configured to releasably attach to a surgical implement. Each of the adapters can be different from one another in shape and/or size, thereby allowing for a particular adapter to be selected by a surgeon (or other medical professional) for optimal desired impacting in a particular surgical procedure being performed on a particular patient's bone. Further, each of the surgical implements configured to be attached to an adapter can be different from one another in shape and/or size, thereby allowing for a particular surgical implement to be selected by a surgeon (or other medical professional) for optimal desired impacting in a particular surgical procedure being performed on a particular patient's bone.

In some embodiments, instead of the surgical implement being releasably attached to the adapter, the surgical implement can be non-releasably attached to the adapter to allow the surgical impacting tool to be used with a variety of different surgical implements by being attachable to a variety of different adapters.

Figure 2:
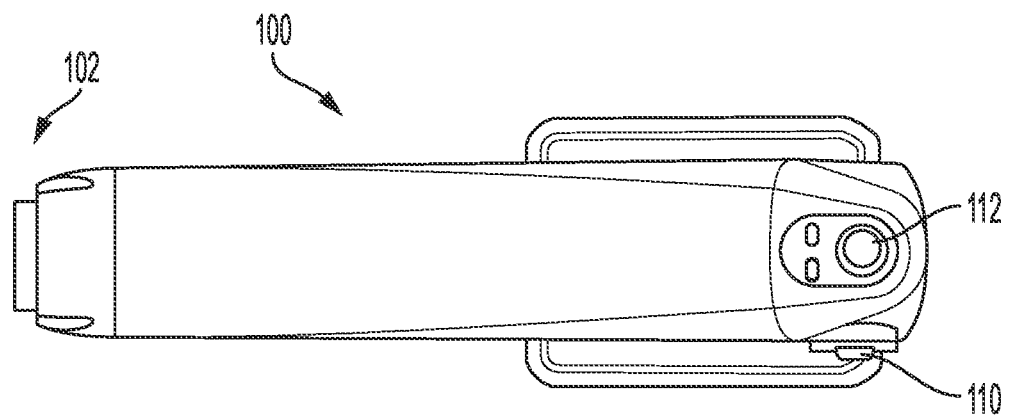
FIG. 2 is a top view of the tool of FIG. 1.
Figure 7:
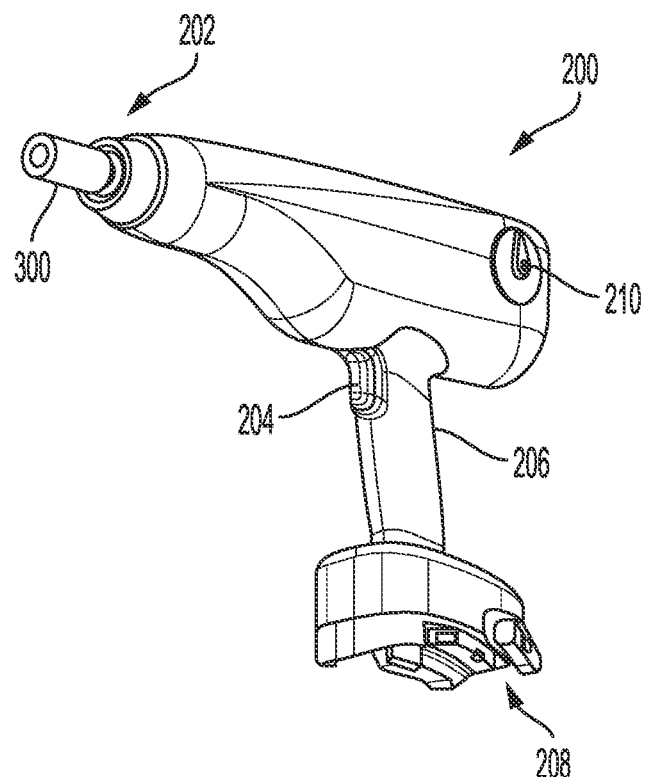
FIG. 7 is a perspective view of the tool and adapter of FIG. 5.
Figure 8:
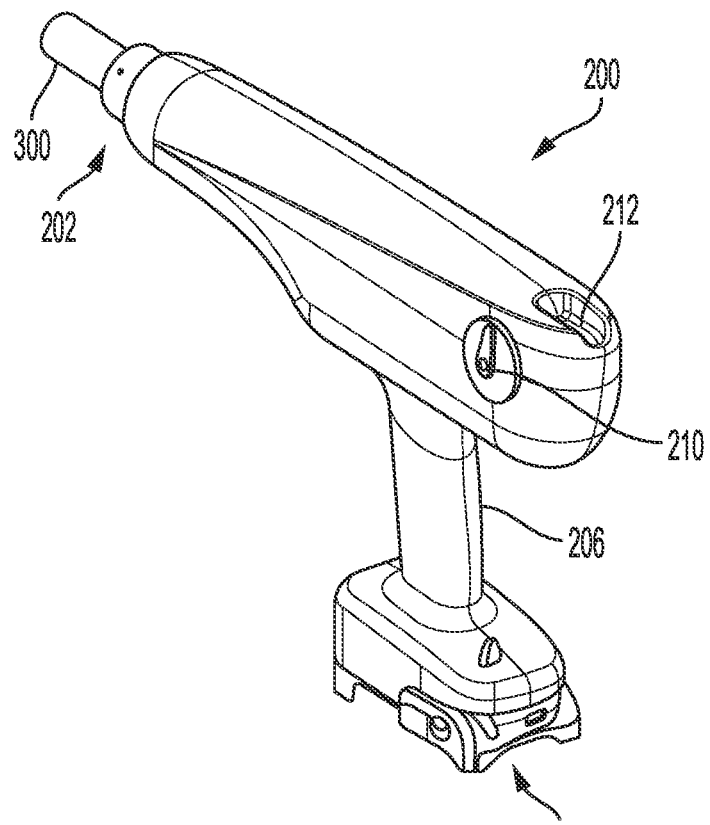
FIG. 8 is another perspective view of the tool and adapter of FIG. 5.

FIGS. 1-3 illustrate one embodiment of a surgical impacting tool 100 including a locking assembly configured to releasably attach to an adapter. The surgical impacting tool 100 is an orthopedic impactor in this illustrated embodiment, but as mentioned above, the surgical impacting tool 100 can be another type of surgical impacting tool. The locking assembly is located at a forward end 102 of the surgical impacting tool 100. Embodiments of the locking assembly are discussed further below.

The surgical impacting tool 100 includes an actuator 104 configured to be actuated to drive a surgical implement attached to an adapter that is releasably attached to the surgical impacting tool 100 via the locking assembly. The actuator 104 in this illustrated embodiment includes a trigger on a handpiece 106 of the surgical impacting tool 100, but other surgical impacting tools can be actuated in other ways. In an exemplary embodiment, the surgical impacting tool 100 is configured to provide forward impacting, in which a forward force is provided by the surgical impacting tool for impacting in a forward direction, and rearward impacting, in which a rearward force is provided by the surgical impacting tool for impacting in a rearward direction. The forward and rearward impacting can be cyclical with sequential repeated forward and rearward impacts. In some embodiments, the surgical impacting tool 100 can be configured to provide only one of forward impacting and rearward impacting.

A power source 108 is configured to releasably attached to the handpiece 106 of the surgical impacting tool 100. The power source 108 includes a battery in this illustrated embodiment, but other power sources are possible. In other embodiments, the surgical impacting tool 100 can be releasably attachable to a power source in another way, such as by being plugged into a power source. In still other embodiments, the power source can be non-releasably attached to the surgical impacting tool 100, such as by a battery being non-removably disposed in the handpiece 106.

The surgical impacting tool 100 includes an energy selector 110 on the handpiece 106 of the surgical impacting tool 100. The energy selector 110 includes a rotary dial in this illustrated embodiment but can have other configurations, such as a lever, a button, etc. The energy selector 110 is configured to allow an energy level to be selected, e.g., high energy or low energy.

The surgical impacting tool 100 includes a frequency control 112 on the handpiece 106 of the surgical impacting tool 100. The frequency control 112 includes a button in this illustrated embodiment but can have other configurations, such as a lever, a rotary dial, etc. The frequency control 112 is configured to allow a frequency of impacts to be selected by a user, e.g., slow impacts or fast impacts.

The surgical impacting tool 100 can have additional or alternate features. Various exemplary embodiments of surgical impacting tools including additional or alternate features are further described in U.S. Pat. Pub. No. 2013/0161050 entitled "Electric Motor Driven Tool For Orthopedic Impacting" published Jun. 27, 2013, U.S. Pat. Pub. No. 2019/0183555 entitled "Orthopedic Adapter For An Electric Impacting Tool" published Jun. 20, 2019, U.S. Pat. Pub. No. 2018/0055552 entitled "Orthopedic Impacting Device Having A Controlled, Repeatable Impact" published Mar. 1, 2018, U.S. Pat. Pub. No. 2018/0055554 entitled "Orthopedic Impacting Device Having A Launched Mass Delivering A Controlled, Repeatable & Reversible Impacting Force" published Mar. 1, 2018, U.S. Pat. No. 8,393,409 entitled "Electric Motor Driven Tool For Orthopedic Impacting" issued Mar. 12, 2013, U.S. Pat. No. 8,936,105 entitled "Electric Motor Driven Tool For Orthopedic Impacting" issued Jan. 20, 2015, and U.S. Pat. No. 8,695,726 entitled "Electric Motor Driven Tool For Orthopedic Impacting" issued Apr. 15, 2014, which are hereby each incorporated by reference in their entirety.

FIGS. 4-8 illustrate another embodiment of a surgical impacting tool 200 including a locking assembly configured to releasably attach to an adapter 300. FIGS. 4-8 show the adapter 300 releasably attached to the surgical impacting tool 200 via the locking assembly. The surgical impacting tool 200 is an orthopedic impactor in this illustrated embodiment, but as mentioned above, the surgical impacting tool 200 can be another type of surgical impacting tool. The surgical impacting tool 200 is generally configured and used similar to the surgical impacting tool 100 of FIG. 1, e.g., includes the locking assembly at a forward end 202 of the surgical impacting tool 200 and includes an actuator 204, a handpiece 206, an energy selector 210 (which is a lever in this illustrated embodiment), and a frequency control 212 (which is a dial in this illustrated embodiment). The surgical impacting tool 200 in this illustrated embodiment is configured at a bottom end 208 of the surgical impacting tool 200 to releasably attach to a power source, similar to the surgical impacting tool 100 being releasably attachable to the power source 108 as discussed above. Embodiments of the locking assembly are discussed further below.

The adapter 300 in this illustrated embodiment is configured to releasably attach to a surgical implement to impact bone. In other embodiments, the adapter 300 can be non-releasably attached to a surgical implement.

Figure 9:
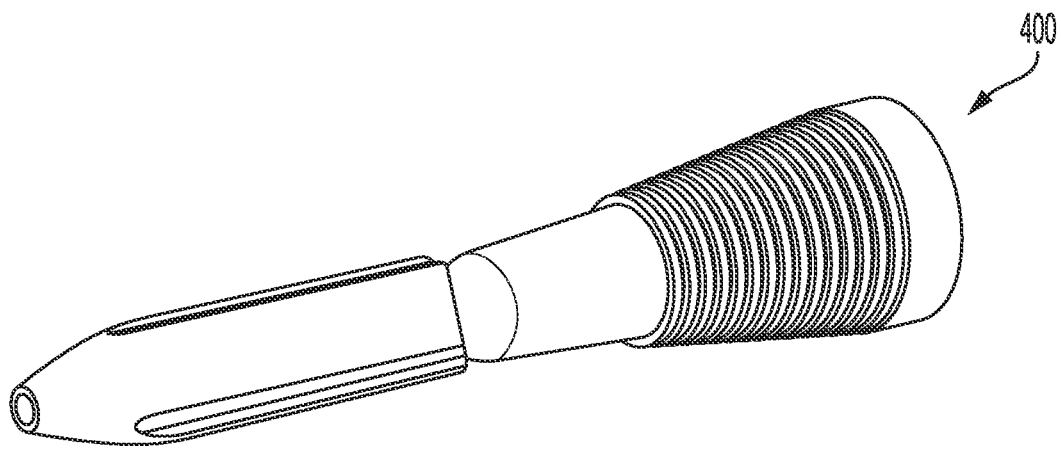
FIG. 9 is a perspective view of one embodiment of a surgical implement.
Figure 10:
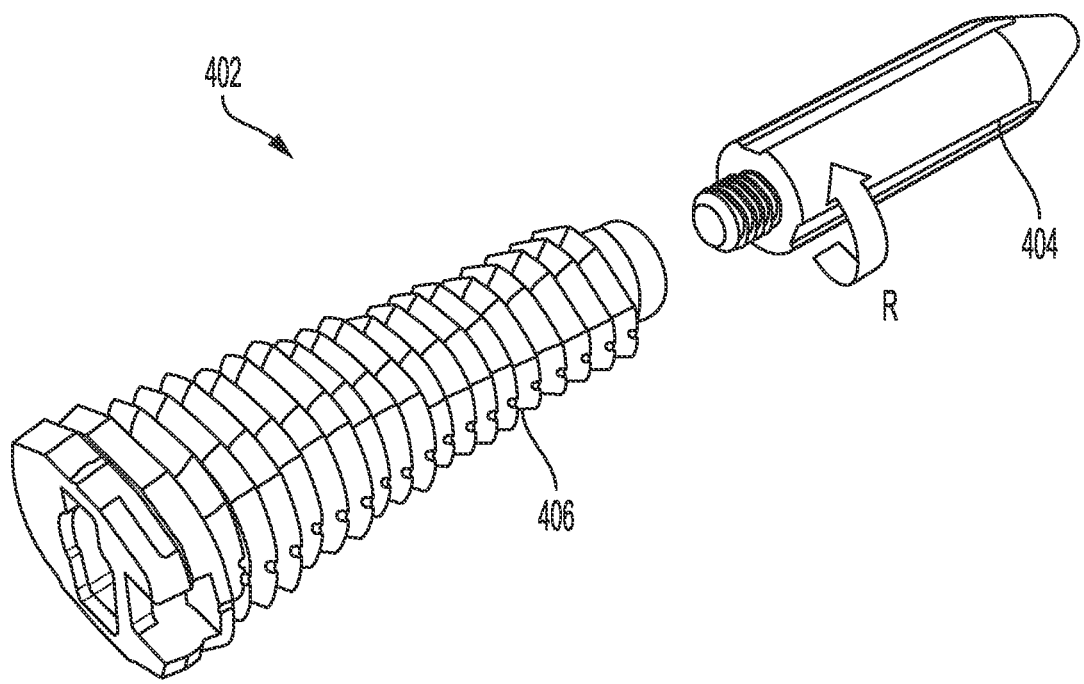
FIG. 10 is a perspective view of another embodiment of a surgical implement.

As mentioned above, various surgical implements such as chisels and broaches can be configured to releasably attach to the adapter 300. FIG. 9 illustrates one embodiment of a surgical implement 400 configured to releasably attach to the adapter 300. The surgical implement 400 in this illustrated embodiment is a tibial broach configured for impacting a tibia. FIG. 10 illustrates another embodiment of a surgical implement 402 configured to releasably attach to the adapter 300. The surgical implement 402 in this illustrated embodiment is a femoral broach configured for impacting a femur. The surgical implement 402 in this illustrated embodiment includes a forward portion 404 and a rearward portion 406 that is configured to releasably attach to the forward portion 404 by rotating the forward portion 404 into the rearward portion 406 as shown by arrow R.

Figure 11:
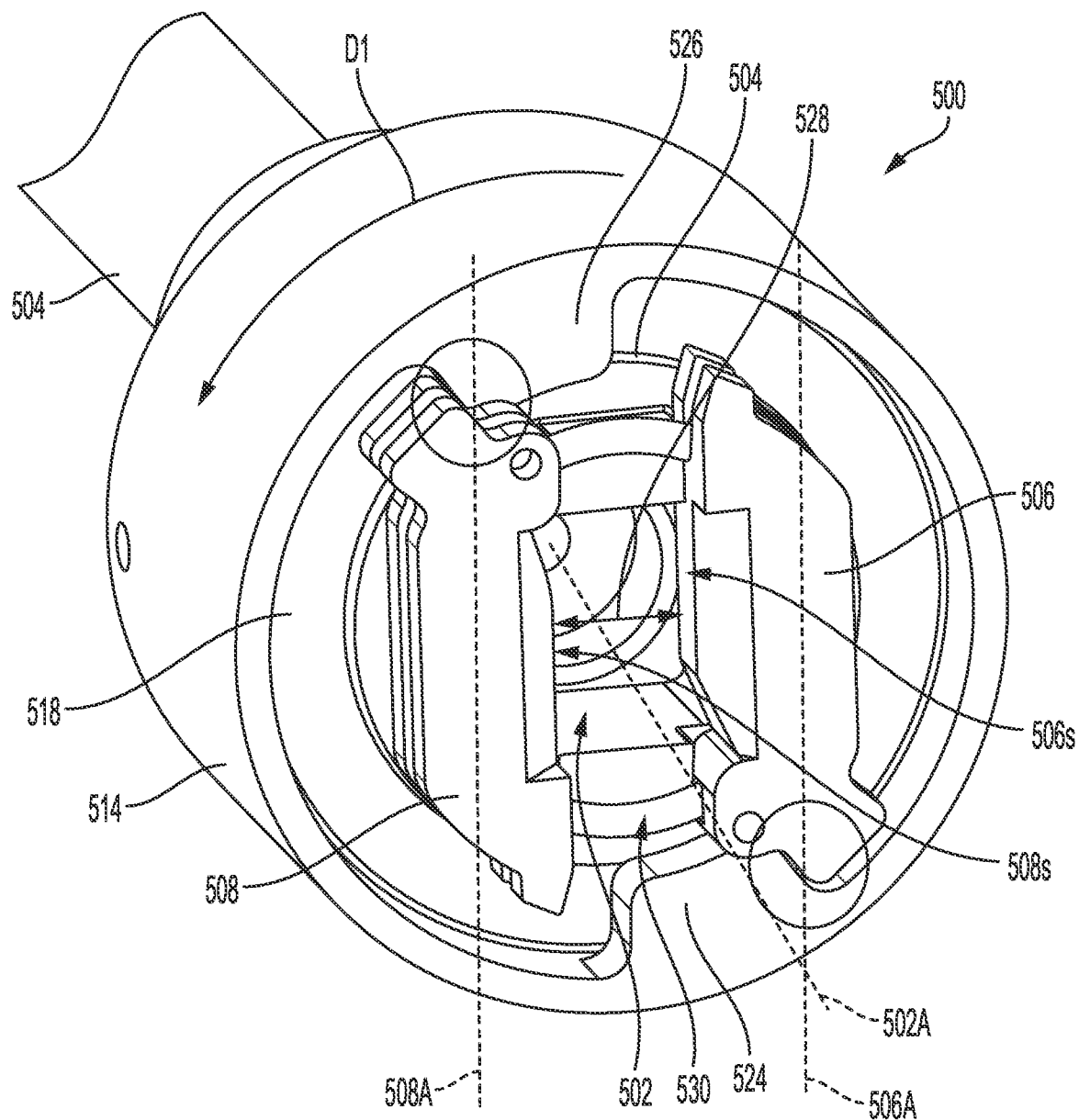
FIG. 11 is a perspective view of one embodiment of a locking assembly.
Figure 12:
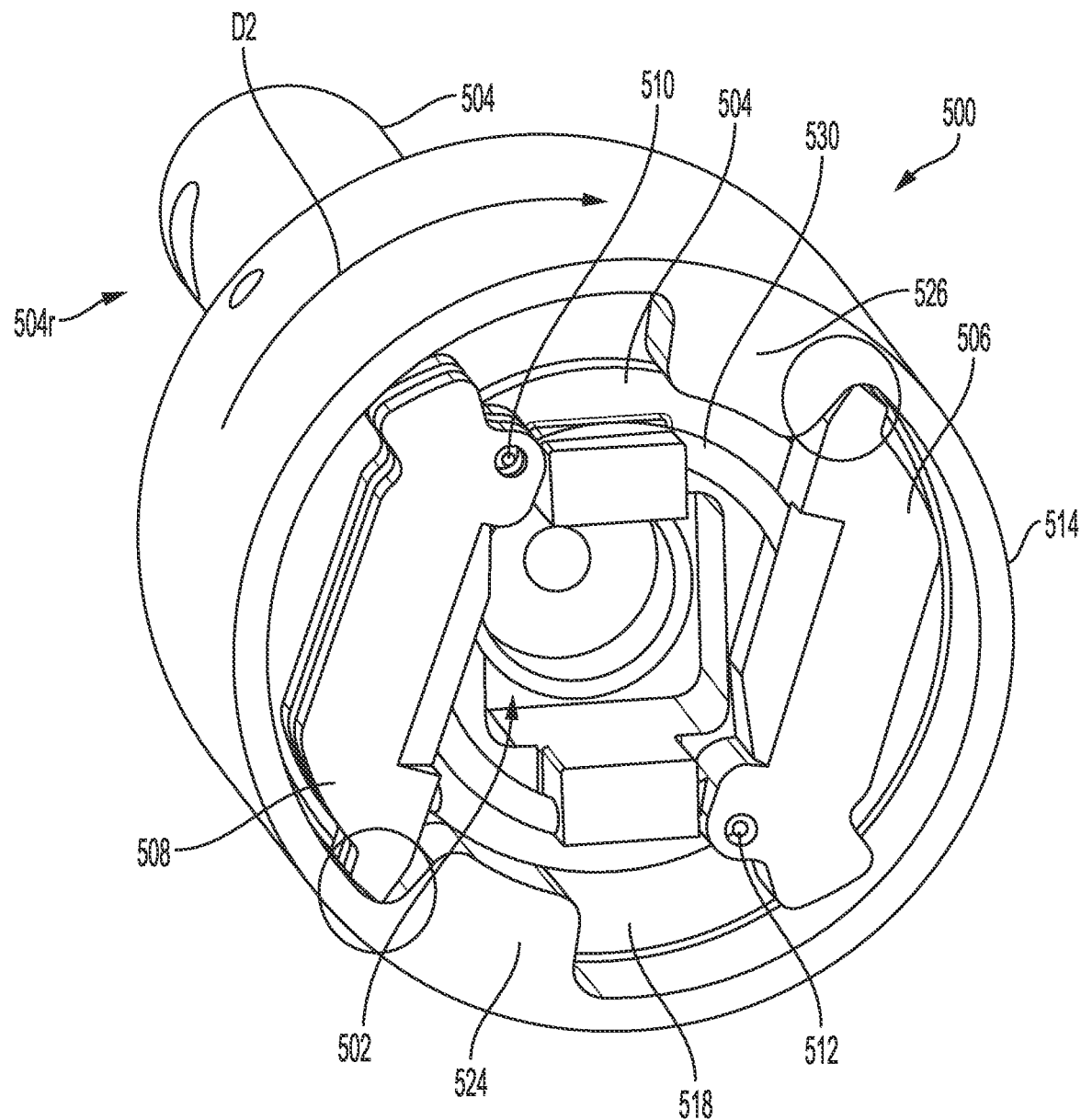
FIG. 12 is a perspective view of the locking assembly of FIG. 11 with a housing thereof rotated.
Figure 13:
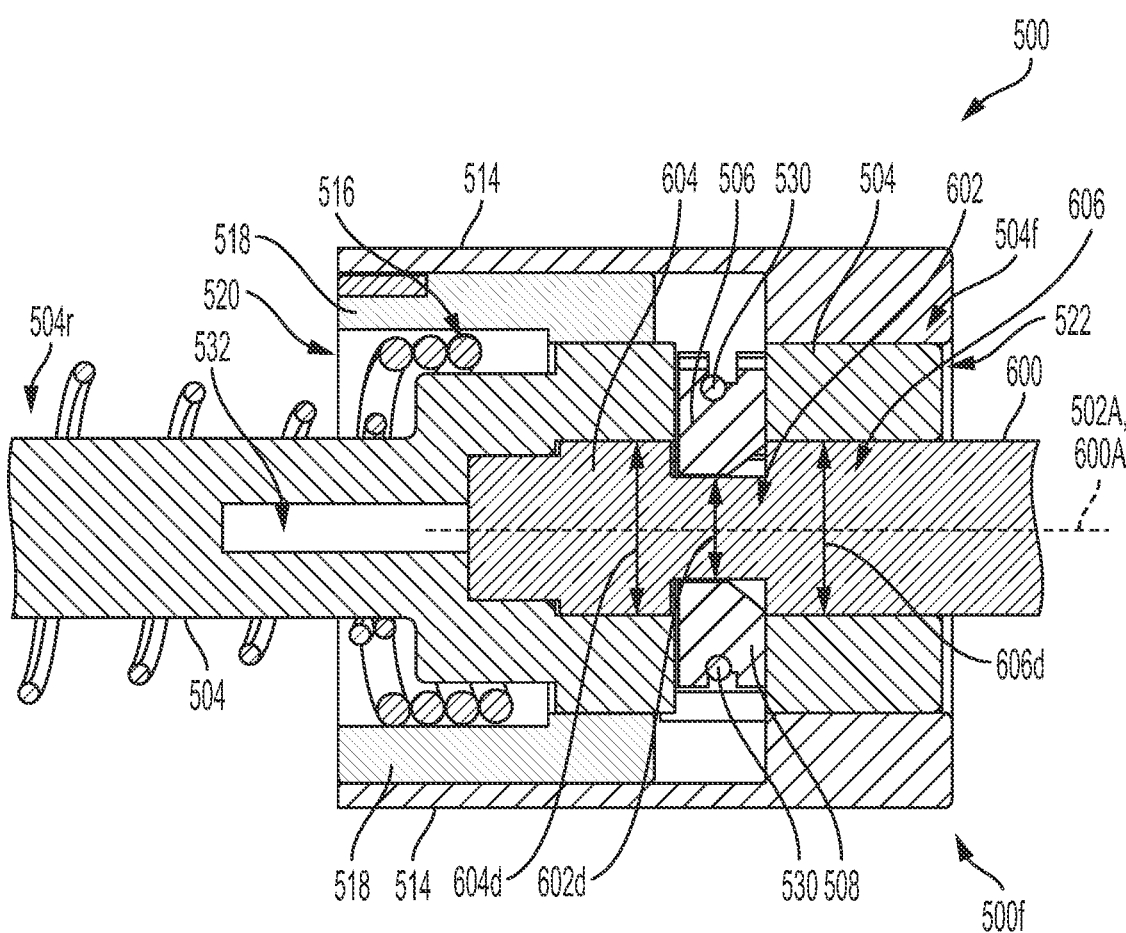
FIG. 13 is a side cross-sectional view of the locking assembly of FIG. 11 with another embodiment of an adapter releasably attached thereto.

As mentioned above, the locking assembly of the surgical impacting tool 100 of FIGS. 1-3 and the locking assembly of the surgical impacting tool 200 of FIGS. 4-8 can have a variety of configurations. FIGS. 11-13 illustrate one embodiment of a locking assembly 500 that can be used as the locking assembly of the surgical impacting tool 100 of FIGS. 1-3, the locking assembly of the surgical impacting tool 200 of FIGS. 4-8, or the locking assembly of another embodiment of a surgical impacting tool. The locking assembly 500 is configured to releasably attach to an adapter, such as the adapter 300 of FIGS. 4-8 or another adapter.

The locking assembly 500 is configured to move between a locked configuration, in which the locking assembly 500 is releasably attached to an adapter, and an unlocked configuration, in which the locking assembly 500 is not releasably attached to an adapter. FIGS. 11 and 13 show the locking assembly 500 in the locked configuration releasably attached to one embodiment of an adapter 600 (the adapter 600 not being shown in FIG. 11 for clarity of illustrating the locking assembly 500), and FIG. 12 shows the locking assembly 500 in the unlocked configuration. The adapter 600 can have a variety of configurations, as discussed herein. The adapter 600 can be configured to releasably attach to a surgical implement or can be non-releasably attached to a surgical implement.

The locking assembly 500 is biased to the locked configuration. The locking assembly 500 is configured to move to the locked configuration in response to the locking assembly's engagement with the adapter 600. The engagement of the adapter 600 with the locking assembly 500 includes the adapter 600 being moved longitudinally, or translationally, into the locking assembly 500. The adapter 600 is thus configured to move in one way, e.g., translationally and not rotationally, to attach to the locking assembly 500. The disengagement of the adapter 600 from the locking assembly 500 includes the locking assembly 500 being rotated relative to the adapter 600 and then the adapter 600 being moved longitudinally, or translationally, relative to the locking assembly 500. The adapter 600 is thus configured to move in the same one way to detach from the locking assembly 500. Rotational motion being needed to allow the adapter 600 to be detached from the locking assembly 500 (and thus from the surgical impacting tool that includes the locking assembly 500) may help prevent the adapter 600 (and a surgical implement attached thereto) from detaching from the surgical impacting tool during impacting since the surgical impacting tool provides a longitudinally directed force for impacting that will not urge rotational movement of the locking assembly 500. The locking assembly 500 needing to rotate relative to the adapter 600 before the adapter 600 is moved translationally relative to the locking assembly 500 (and thus relative to the surgical impacting tool that includes the locking assembly 500) to be detached from the locking assembly 500 (and thus from the surgical impacting tool that includes the locking assembly 500) may help prevent a process of removing the adapter 600 (and a surgical implement attached thereto) from the locking assembly 500 (and thus from the surgical impacting tool that includes the locking assembly 500) from starting until a user intentionally rotates the locking assembly 500 since the surgical impacting tool's longitudinally directed force for impacting that will not urge rotational movement of the locking assembly 500.

The locking assembly 500 includes a cavity 502 configured to seat a rearward portion of an adapter therein. The cavity 502 is located at a forward end 500f of the locking assembly 500 and thus at a forward end of the surgical impacting tool that includes the locking assembly 500. The cavity 502 is formed in a base 504 of the locking assembly 500. A forward portion 504f of the base 504 has the cavity 502 formed therein such that the cavity 502 is accessible at the forward end 500f of the locking assembly 500.

A rearward end 504r of the base 504 is configured to be operably coupled to a drive mechanism of the surgical impacting tool that includes the locking assembly 500 to allow the drive mechanism to provide a longitudinally directed force to the base 504 to drive impacting of a surgical implement attached to the adapter 600 that is attached to the locking mechanism 500. The drive mechanism can have a variety of configurations. Various embodiments of drive mechanisms are further described in previously mentioned U.S. Pat. Pub. No. 2013/0161050 entitled "Electric Motor Driven Tool For Orthopedic Impacting" published Jun. 27, 2013, U.S. Pat. Pub. No. 2019/0183555 entitled "Orthopedic Adapter For An Electric Impacting Tool" published Jun. 20, 2019, U.S. Pat. Pub. No. 2018/0055552 entitled "Orthopedic Impacting Device Having A Controlled, Repeatable Impact" published Mar. 1, 2018, U.S. Pat. Pub. No. 2018/0055554 entitled "Orthopedic Impacting Device Having A Launched Mass Delivering A Controlled, Repeatable & Reversible Impacting Force" published Mar. 1, 2018, U.S. Pat. No. 8,393,409 entitled "Electric Motor Driven Tool For Orthopedic Impacting" issued Mar. 12, 2013, U.S. Pat. No. 8,936,105 entitled "Electric Motor Driven Tool For Orthopedic Impacting" issued Jan. 20, 2015, and U.S. Pat. No. 8,695,726 entitled "Electric Motor Driven Tool For Orthopedic Impacting" issued Apr. 15, 2014.

The cavity 502 has a square cube shape in this illustrated embodiment but can have another shape, e.g., hemispherically shaped, rectangular cube shaped, irregularly shaped, etc. A size and shape of the cavity 502 corresponds to a size and shape of a rearward portion of the adapter 600 to allow the rearward portion of the adapter 600 to be seated in the cavity 502 and locked therein, as shown in FIG. 13 and as discussed further below.

The locking assembly 500 is configured to seat the adapter 600 in the cavity 502 at each of a plurality of predetermined angular orientations relative to the locking assembly 500. A surgical implement operatively coupled to the locking assembly 500 via the adapter 600, and thus also operatively coupled to the surgical impacting tool that includes the locking assembly 500, can thus be attached to the surgical impacting tool at a plurality of predetermined angular orientations relative to the surgical impacting tool. Depending on one or more factors such as surgeon preference, which hand (left or right) of a user is holding the surgical impacting tool, which bone of a patient the surgical implement will be impacting, and a position of a patient relative to a user of the surgical impacting tool, a certain angular orientation of the surgical implement may be more desirable than another angular orientation of the surgical implement. In an exemplary embodiment, each of the predetermined angular orientations is about ninety degrees apart from one another. A person skilled in the art will appreciate that a value may not be precisely at a value but nevertheless be considered to be about that value due to any number of factors, such as manufacturing tolerances and sensitivity of measurement equipment.

In this illustrated embodiment, the locking assembly 500 is configured to seat the adapter in the cavity 502 at four predetermined angular orientations relative to the locking assembly 500: about zero degrees, about ninety degrees, about one hundred eighty degrees, and about two hundred seventy degrees. Providing four predetermined angular orientations may simplify manufacturing of the base 504 that includes the cavity 502 and/or may help ensure that whether the surgical impacting tool that includes the locking assembly 500 is being held by a left hand or a right hand, and whether or not the surgical impacting tool is being held upright during impacting, the surgical implement operably coupled to the surgical impacting tool can be at a convenient angle for impacting bone. The square cube shape of the cavity 502 allows for the four predetermined angular orientations each about ninety degrees apart from one another. Other four-sided shapes, e.g., rectangle, of the cavity 502 similarly allow for four predetermined angular orientations. Other cavity shapes not having four sides will define another number of predetermined angular orientations or will not define any predetermined angular orientations. For example, a spherical cavity shape will not define any predetermined angular orientations. For another example, a five-sided cavity shape defines five predetermined angular orientations. For another example, a three-sided cavity shape defines three predetermined angular orientations. For yet another example, an eight-sided cavity shape defines eight predetermined angular orientations.

The locking assembly 500 includes a first pawl 506 and a second pawl 508 that are each configured to rotate relative to the base 504 of the locking assembly 500 to lock the adapter 600 to the surgical impacting tool that includes the locking assembly 500. The first pawl 506 is attached to the base 504 at a first pivot point 510, e.g., using a pivot pin or other mechanism, about which the first pawl 506 is configured to rotate relative to the base 504. The second pawl 508 is attached to the base 504 at a second pivot point 512, e.g., using a pivot pin or other mechanism, about which the second pawl 508 is configured to rotate relative to the base 504. The first and second pivot points 510, 512 are on opposed sides of the base 504. The first and second pawls 506, 508 are configured to simultaneously pivot relative to the base 504 at their respective pivot points 510, 512.

The first and second pawls 506, 508 are positioned relative to the cavity 502 formed in the base 504 to allow the first and second pawls 506, 508 to engage the adapter 600 inserted into the cavity 502. The first and second pawls 506, 508 are opposed to one another on opposite sides of the cavity 502. The first pawl 506 defines a first longitudinal axis 506A that is substantially perpendicular to a longitudinal axis 502A (see FIGS. 11 and 13) defined by the cavity 502 with the locking assembly 500 in the locked configuration. The second pawl 508 defines a second longitudinal axis 508A that is substantially perpendicular to the longitudinal axis 502A defined by the cavity 502 with the locking assembly 500 in the locked configuration. The locking assembly 500 moving between the unlocked configuration and the locked configuration, and with the locking assembly 500 in the unlocked configuration, the first and second longitudinal axes 506A, 508A are not substantially perpendicular to the longitudinal axis 502A defined by the cavity 502. The first and second longitudinal axes 506A, 508A are substantially parallel to one another with the locking assembly 500 in the unlocked configuration, with the locking assembly 500 in the locked configuration, and during movement of the locking assembly 500 between the locked and unlocked configurations. A person skilled in the art will appreciate that axes may not be precisely perpendicular or precisely parallel but nevertheless be considered to be substantially perpendicular or substantially parallel due to any number of factors, such as manufacturing tolerances and sensitivity of measurement equipment.

The locking assembly 500 includes a housing 514 that is operatively coupled to the first pawl 506 and the second pawl 508. The locking assembly 500 also includes a first biasing element 516 (see FIG. 13) configured to bias the housing 514 in a first direction D1 (see FIG. 11), which is counterclockwise in this illustrated embodiment. The first biasing element 516 biases the housing 514 to the locked configuration of the locking assembly 500. The locking assembly 500 includes a support 518 that seats the first biasing element 516 therein, as shown in FIG. 13. The support 518 is a tubular member having an inner passageway 520 extending therethrough. The first biasing element 516 is disposed in the inner passageway 520. The support 518 is in fixed relation to the housing 514. The support 518 can be integrally formed with the housing 514 or can be a separate element that is fixedly attached to the housing 514.

The housing 514 is a tubular member having an inner passageway 522 extending therethrough. The cavity 502 formed in the base 504, the forward portion 504*f* of the base 504, the first and second pawls 506, 508, and the first biasing element 516 are located in the inner passageway 522. The base 504 extends rearwardly from the housing 514 with the rearward portion 504r of the base 504 being located outside and rearward of the housing 514.

The housing 514 includes first and second bosses 524, 526 that each extend radially inward. The first and second bosses 524, 526 are configured to operatively engage the first and second pawls 506, 508 to cause pivoting of the first and second pawls 506, 508 at their respective pivot points 510, 512, as discussed further below. As shown in FIG. 11, with the locking assembly 500 in the locked configuration, a first side surface of the first boss 524 abuts a first cam surface of the first pawl 506, and a first side surface of the second boss 526 abuts a first cam surface of the second pawl 508. The housing 514 being biased in the first direction D1 by the first biasing element 516 urges the first side surface of the first boss 524 into abutting contact with the first cam surface of the first pawl 506 and urges the first side surface of the second boss 526 into abutting contact with the first cam surface of the second pawl 508.

The locking assembly 500 is configured to automatically move to the locked configuration in response to the locking assembly's engagement with the adapter 600. In an exemplary embodiment, the adapter 600 being moved into the cavity 502 along the longitudinal axis 502A defined by the cavity 502 is configured to cause the locking assembly 500 to automatically move to the locked configuration. The adapter 600 can be moved into the cavity 502 by moving the adapter 600 in a rearward direction relative to the locking assembly 500, by moving the locking assembly 500 forward relative to the adapter 600, or by both moving the adapter 600 in a rearward direction relative to the locking assembly 500 and moving the locking assembly 500 forward relative to the adapter 600.

As shown in FIGS. 11-13, the first and second pawls 506, 508 are located at an intermediate position along an axial length of the cavity 502. Thus, in moving into the cavity 502 and before being seated and locked therein, the adapter 600 encounters the first and second pawls 506, 508. First and second side surfaces 506s, 508s of the first and second pawls 506, 508 face one another with the locking assembly 500. A gap 528 is defined between the pawl side surfaces 506s, 508s. With the locking assembly 500 in the locked configuration, a minimum width of the gap 528 is less than a width of the cavity 502 rearward of the pawls 506, 508 and is less than a width of the rearward portion of the adapter 600 that is being inserted into the cavity 502.

The adapter 600 being moved longitudinally into the cavity 502 causes the adapter 600 to engage the first and second side surfaces 506s, 508s. Because the adapter 600 is wider than the gap 528, and because the first and second pawls 506, 508 are movably attached to the base 504 having the cavity 502 formed therein, the adapter 600 can move rearwardly through the gap 528 by slidingly engaging the pawl side surfaces 506s, 508s, which causes the first and second pawls 506, 508 to pivot at their respective pivot points 510, 512 and thereby widen the gap 528. The adapter 600 can thus be moved longitudinally into the cavity 502 until a rearward facing surface of the adapter 600 abuts a forward facing surface of the base 604 that defines a rearward end of the cavity 502.

As shown in FIG. 13, the rearward portion of the adapter 600 includes a reduced diameter portion 602 having a smaller diameter 602d than a diameter 604d of a portion 604 of the adapter 600 rearward of the reduced diameter portion 602 and than a diameter 606d of a portion 606 of the adapter 600 forward of the reduced diameter portion 602. The diameter 604d of the portion 604 of the adapter 600 rearward of the reduced diameter portion 602 is moved rearwardly past the first and second pawls 506, 508. When the reduced diameter portion 602 of the adapter 600 becomes axially aligned with the first and second pawls 506, 508, the first and second pawls 506, 508 are no longer being urged outwardly by the adapter 600 and are allowed to freely pivot inwardly toward their initial, default position (shown in FIG. 11). The first and second pawls 506, 508 will thus become seated in the reduced diameter portion 602, as shown in FIG. 13. The first and second pawls 506, 508 being seated in the reduced diameter portion 602 of the adapter 600 prevents the adapter 600 from moving longitudinally relative to the locking assembly 500 (and thus relative to the surgical impacting tool that includes the locking assembly 500).

The locking assembly 500 includes a friction member 530 configured to add resistance to the rotational movement of the first and second pawls 506, 508. The friction member 530 in this illustrated embodiment includes an o-ring but can have other configurations. The friction member 530 may help hold the first and second pawls 506, 508 in position when the locking assembly 500 is in its unlocked configuration and in its locked configuration. A user seating the adapter 600 in the cavity 502 may be able to feel the resistance, which may help the user know that the adapter 600 is being properly attached to the locking assembly 500 (and thus to the surgical impacting tool that includes the locking assembly 500).

As mentioned above, the locking assembly 500 is configured to move from the locked configuration to the unlocked configuration. In an exemplary embodiment, the housing 514 of the locking assembly 500 being rotated about the longitudinal axis 502A defined by the cavity 502 (and thus about the adapter's longitudinal axis 600A coaxial therewith) relative to the adapter 600 and to the base 504 is configured to cause the locking assembly 500 to move from the locked configuration to the unlocked configuration to allow the adapter 600 to then be moved longitudinally along the longitudinal axis 502A defined by the cavity 502 (and thus about the adapter's longitudinal axis 600A coaxial therewith). The adapter 600 can be moved out of the cavity 502 by moving the adapter 600 in a forward direction relative to the locking assembly 500, by moving the locking assembly 500 rearward relative to the adapter 600, or by both moving the adapter 600 in a forward direction relative to the locking assembly 500 and moving the locking assembly 500 rearward relative to the adapter 600.

With the locking assembly 500 in the locked position so as to be releasably attached to the adapter 600, the housing 514 is rotated in a second direction D2, as shown in FIG. 12, that is opposite to the first direction D1 in which the housing 514 is biased. The rotation of the housing 514 in the second direction D2 also causes the support 518 fixedly attached thereto to rotate in the second direction D2, which is clockwise in this illustrated embodiment. The rotation of the housing 514 causes the first and second bosses 524, 526 of the housing 514 to rotate. The rotation of the first and second bosses 524, 526 in the second direction D2 causes the first side surface of the first boss 524 to move out of abutting contact with the first cam surface of the first pawl 506 and causes the first side surface of the second boss 526 to move out of abutting contact with the first cam surface of the second pawl 508. Continued rotation of the first and second bosses 524, 526 in the second direction D2 causes a second side surface of the first boss 524 to abut a second side surface of the second pawl 508 and causes a second side surface of the second boss 526 to abut a second side surface of the first pawl 506. Thus, the first boss 524 moves out of contact with the first pawl 506 and into contact with the second pawl 508, and the second boss 526 moves out of contact with the second pawl 508 and into contact with the first pawl 506. The rotation of the first boss 524 in the second direction D2 pushes the second pawl 508 to cause rotation of the second pawl 508 about the second pivot point 512, and rotation of the second boss 526 in the second direction D2 pushes the first pawl 506 to cause rotation of the first pawl 506 about the first pivot point 510. The gap 528 between the first and second pawls 506, 508 thus increases, as shown in FIG. 12. The widened gap 528 allows for the adapter 600 to be moved longitudinally out of the cavity 502 since the diameter 604d of the adapter's portion 604 rearward of the reduced diameter portion 602 can now pass through the gap 528.

After the adapter 600 has been removed from the cavity 502, the housing 514 can be released, thereby allowing the housing 514 to rotate in the first direction D1 under force of the biasing element 516 to return the locking assembly 500 to its initial configuration. The housing 514 can be manually moved in the first direction D1 to help the housing's rotational movement, or the housing 514 can be allowed to move in the first direction D1 fully under force provided by the biasing element 516.

As shown in FIG. 13, the base 504 includes a blind hole 532 rearward of and in communication with the cavity 502. A second biasing element (not shown), e.g., a coil spring, an elastomeric material, a spring-loaded plunger, etc., can be disposed in the blind hole 532. The second biasing element can be configured to provide a forward biasing force and can be configured to engage the rearward facing surface of the adapter 600 when the locking assembly 500 is locked to the adapter 600. The second biasing element can thus be configured to urge the adapter 600 in a forward direction after the housing 514 has been rotated in the second direction D2, which may help a user remove the adapter 600 from the cavity 502 by pushing the adapter 600 partially out of the cavity 502. The locking assembly 500 can omit the blind hole 532 if a second biasing element is not present.

FIGS. 14-20 illustrate another embodiment of a locking assembly 700 that can be used as the locking assembly of the surgical impacting tool 100 of FIGS. 1-3, the locking assembly of the surgical impacting tool 200 of FIGS. 4-8, or the locking assembly of another embodiment of a surgical impacting tool. The locking assembly 700 is illustrated as being releasably attachable to the adapter 600 of FIG. 13 but can be releasably attached to another adapter, such as the adapter 300 of FIGS. 4-8 or another adapter.

Figure 18:
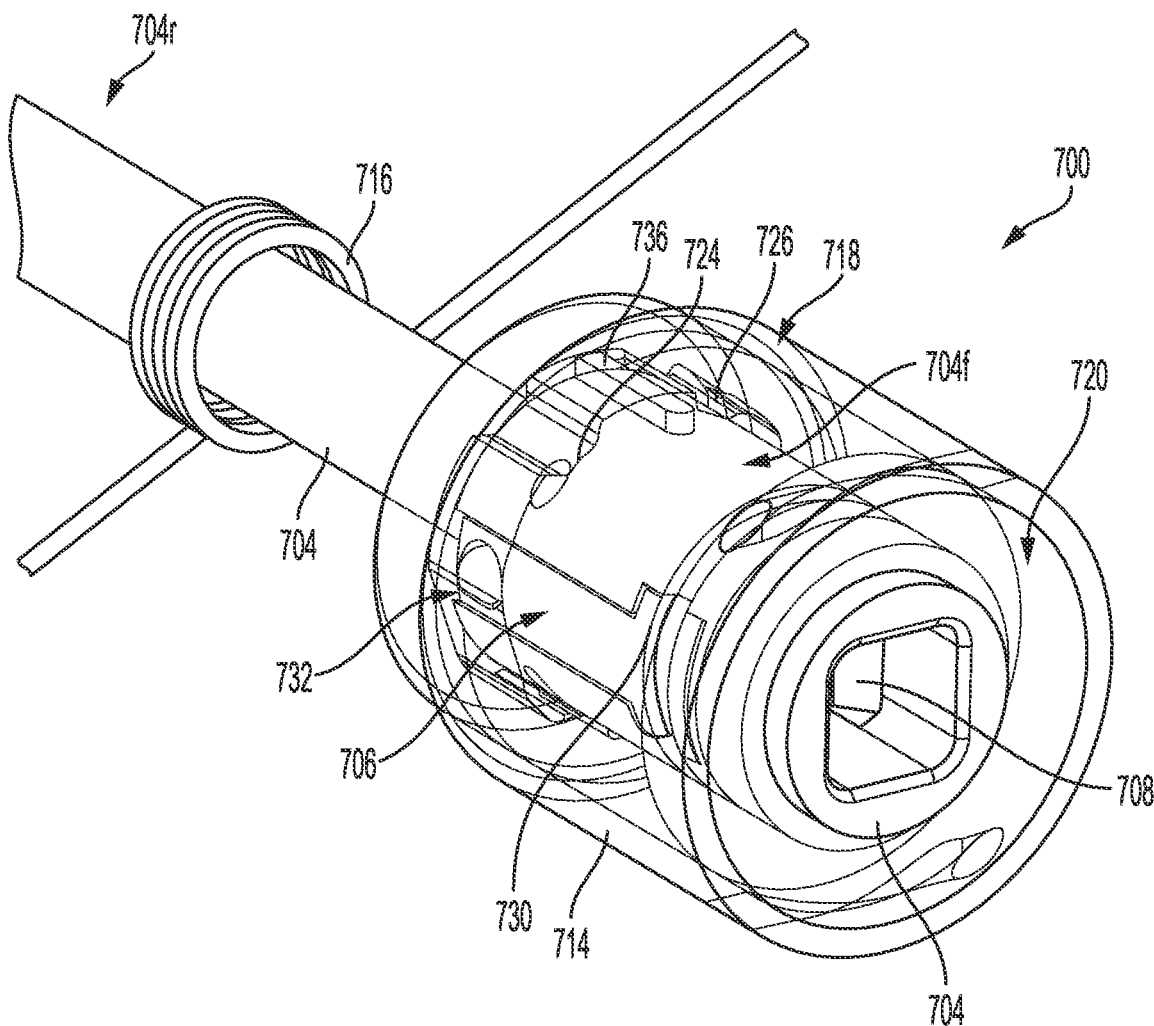
FIG. 18 is a perspective view of the locking assembly of FIG. 14 with a housing thereof rotated.
Figure 19:
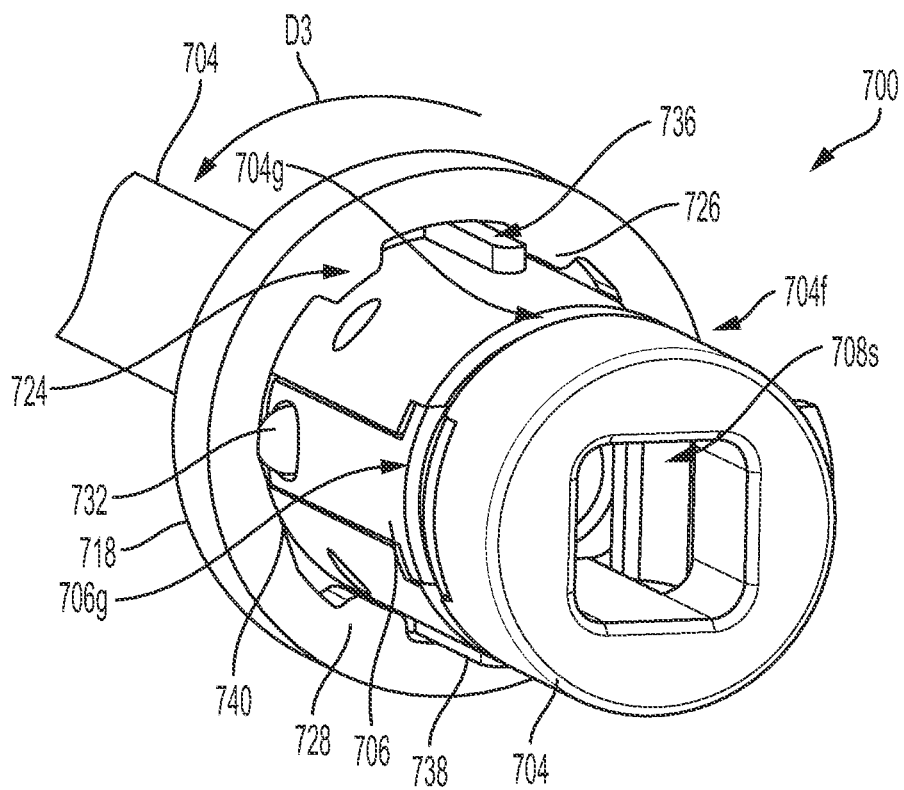
FIG. 19 is another perspective view of the locking assembly of FIG. 18.
Figure 20:
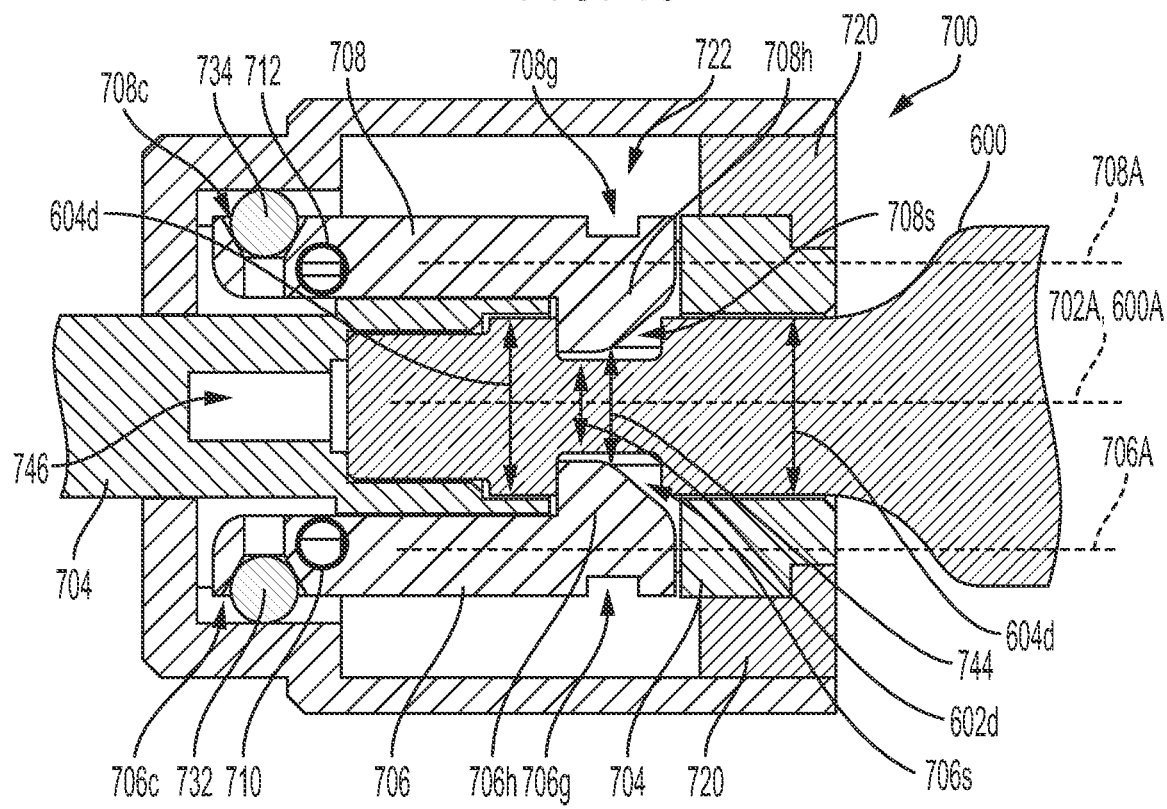
FIG. 20 is a side cross-sectional view of the locking assembly of FIG. 18 with the adapter of FIG. 17 releasably attached thereto.

The locking assembly 700 is configured to move between a locked configuration, in which the locking assembly 700 is releasably attached to the adapter 600 (or another adapter), and an unlocked configuration, in which the locking assembly 700 is not releasably attached to the adapter 600 (or any other adapter). FIGS. 14-17 show the locking assembly 700 in the unlocked configuration, and FIGS. 18-20 show the locking assembly 700 in the locked configuration and releasably attached to the adapter 600 (the adapter 600 not being shown in FIGS. 18 and 19 for clarity of illustrating the locking assembly 700).

The locking assembly 500 of FIGS. 11-13 includes rotary lock pawls 506, 508 that are configured to rotate about the longitudinal axes 502A, 600A of the locking assembly's cavity 502 and the adapter 600, respectively, to facilitate unlocking of the adapter 600 from the locking assembly 500 and thus from the surgical impacting tool that includes the locking assembly 500. The locking assembly 700 of FIGS. 14-20 includes pivoting lock pawls 706, 708 that are configured to pivot away from a longitudinal axis 702A of the locking assembly's cavity 702 and the longitudinal axis 600A of the adapter 600, which is coaxial with the cavity's longitudinal axis 702A, to facilitate unlocking of the adapter 600 from the locking assembly 700 and thus from the surgical impacting tool that includes the locking assembly 700.

The locking assembly 700 is biased to the locked configuration. The locking assembly 500 is configured to move to the locked configuration in response to the locking assembly's engagement with the adapter 700. The engagement of the adapter 600 with the locking assembly 700 includes the adapter 600 being moved longitudinally, or translationally, into the locking assembly 700. The adapter 600 is thus configured to move in one way, e.g., translationally and not rotationally, to attach to the locking assembly 700. The disengagement of the adapter 600 from the locking assembly 700 includes the locking assembly 700 being rotated relative to the adapter 600 and then the adapter 600 being moved longitudinally, or translationally, relative to the locking assembly 700. The adapter 600 is thus configured to move in the same one way to detach from the locking assembly 700. Rotational motion being needed to allow the adapter 600 to be detached from the locking assembly 700 (and thus from the surgical impacting tool that includes the locking assembly 700) may help prevent the adapter 600 (and a surgical implement attached thereto) from detaching from the surgical impacting tool during impacting since the surgical impacting tool provides a longitudinally directed force for impacting that will not urge rotational movement of the locking assembly 700. The locking assembly 700 needing to rotate relative to the adapter 600 before the adapter 600 is moved translationally relative to the locking assembly 700 (and thus relative to the surgical impacting tool that includes the locking assembly 700) to be detached from the locking assembly 700 (and thus from the surgical impacting tool that includes the locking assembly 700) may help prevent a process of removing the adapter 600 (and a surgical implement attached thereto) from the locking assembly 700 (and thus from the surgical impacting tool that includes the locking assembly 700) from starting until a user intentionally rotates the locking assembly 700 since the surgical impacting tool's longitudinally directed force for impacting that will not urge rotational movement of the locking assembly 700.

The locking assembly 700 includes a cavity 702 configured to seat a rearward portion of an adapter therein. The cavity 702 is located at a forward end 700f of the locking assembly 700 and thus at a forward end of the surgical impacting tool that includes the locking assembly 700. The cavity 702 is formed in a base 704 of the locking assembly 700. A forward portion 704f of the base 704 has the cavity 702 formed therein such that the cavity 702 is accessible at the forward end 700f of the locking assembly 700.

A rearward end 704r of the base 704 is configured to be operably coupled to a drive mechanism of the surgical impacting tool that includes the locking assembly 700 to allow the drive mechanism to provide a longitudinally directed force to the base 704 to drive impacting of a surgical implement attached to the adapter 600 that is attached to the locking mechanism 700. The drive mechanism can have a variety of configurations, as discussed above.

The cavity 702 has a square cube shape in this illustrated embodiment but can have another shape, e.g., hemispherically shaped, rectangular cube shaped, irregularly shaped, etc. As discussed above, the square shape of the cavity 702 allows the locking assembly 700 to seat the adapter 600 in the cavity 702 at each of four predetermined angular orientations relative to the locking assembly 700, but other shapes of the cavity 702 corresponding to other predetermined angular orientations (or no predetermined angular orientations) are possible. A size and shape of the cavity 702 corresponds to a size and shape of a rearward portion of the adapter 600 to allow the rearward portion of the adapter 600 to be seated in the cavity 702 and locked therein, as shown in FIG. 20 and as discussed further below.

The first pawl 706 and the second pawl 708 are each configured to pivot relative to the base 704 of the locking assembly 700 to lock the adapter 600 to the surgical impacting tool that includes the locking assembly 700. The first pawl 706 is attached to the base 704 at a first pivot point 710, e.g., using a pivot pin or other mechanism, about which the first pawl 706 is configured to rotate relative to the base 704. The second pawl 708 is attached to the base 704 at a second pivot point 712, e.g., using a pivot pin or other mechanism, about which the second pawl 708 is configured to rotate relative to the base 704. The first and second pivot points 710, 712 are on opposed sides of the base 704. The first and second pawls 706, 708 are configured to simultaneously pivot relative to the base 704 at their respective pivot points 710, 712.

The first and second pawls 706, 708 are positioned relative to the cavity 702 formed in the base 704 to allow the first and second pawls 706, 708 to engage the adapter 600 inserted into the cavity 702. The first and second pawls 706, 708 are opposed to one another on opposite sides of the cavity 702. The first pawl 706 defines a first longitudinal axis 706A that is substantially parallel to the longitudinal axis 702A defined by the cavity 702 with the locking assembly 700 in the locked configuration (see FIG. 20). The second pawl 708 defines a second longitudinal axis 708A that is substantially parallel to the longitudinal axis 702A defined by the cavity 702 with the locking assembly 700 in the locked configuration (see FIG. 20). The first and second longitudinal axes 706A, 708A are thus substantially parallel to one another with the locking assembly 700 in the locked configuration. The locking assembly 700 moving between the unlocked configuration and the locked configuration, and with the locking assembly 700 in the unlocked configuration, the first and second longitudinal axes 706A, 708A are not substantially parallel to one another or to the longitudinal axis 702A defined by the cavity 702 (see FIG. 17).

The first and second pawls 706, 708 are biased to the locked configuration. The locking mechanism 700 includes a first biasing element 730 (see FIG. 18) configured to bias the first and second pawls 706, 708 to the locked configuration. The first biasing element 730 includes an o-ring in this illustrated embodiment but can include another biasing element, such as an elastomeric band, etc. The first pawl 706 includes a groove 706g formed in an outwardly facing surface thereof that is configured to seat the first biasing element 730 therein. The second pawl 708 includes a groove 708g formed in an outwardly facing surface thereof that is configured to seat the first biasing element 730 therein. The base 704 includes a groove 704g formed in an outwardly facing surface thereof that is configured to seat the first biasing element 730 therein. The groove 704g extends circumferentially around the base 704 such that the first biasing element 730 surrounds a circumference of the base 704.

The locking assembly 700 includes first and second cam followers 732, 734 configured to facilitate pivoting of the first and second pawls 706, 708. The first and second cam followers 732, 734 each include a ball bearing in this illustrated embodiment, but other cam followers are possible. The first cam follower 732 is operatively coupled to the first pawl 706, and the second cam follower 734 is operatively coupled to the second pawl 708. The first pawl 706 includes a cavity 706c configured to seat the first cam follower 732 therein. The first pawl's cavity 706c is formed in the outwardly facing surface of the first pawl 706. The second pawl 708 includes a cavity 708c configured to seat the second cam follower 734 therein. The second pawl's cavity 708c is formed in the outwardly facing surface of the second pawl 708.

The locking assembly 700 includes a housing 714. The housing 714 is a tubular member having an inner passageway 722 extending therethrough. The cavity 702 formed in the base 704, the forward portion 704f of the base 704, and the first and second pawls 706, 708 are located in the inner passageway 722. The base 704 extends rearwardly from the housing 714 with the rearward portion 704r of the base 704 being located outside and rearward of the housing 714.

The locking assembly 700 includes an end cap 720 that seats a forward end of the base 704 therein, as shown in FIGS. 16-18 and 20. The end cap 720 is a tubular member having an inner passageway 720i extending therethrough. The forward end of the base 704 is disposed in the inner passageway 720i. The end cap 720 is disposed in the housing 714, e.g., in the inner passageway 722 thereof, and is in fixed relation to the housing 714.

The locking assembly 700 also includes a second biasing element 716 configured to bias the housing 714 in a first direction D3 (see FIG. 19), which is counterclockwise in this illustrated embodiment. The second biasing element 716 biases the housing 714 to the locked configuration of the locking assembly 700.

The housing 714 is operatively coupled to a collar 718 of the locking assembly 700. The collar 718 is operatively coupled to the first pawl 706 and the second pawl 708. The collar 718 is in fixed relation to the housing 714. The collar 718 can be integrally formed with the housing 714 or can be a separate element that is fixedly attached to the housing 714. The collar 718 is a tubular member having an inner passageway 718i extending therethrough. The base 704 extends through the collar's inner passageway 718i.

The collar 718 includes first, second, third, and fourth bosses 724, 726, 728 that each extend radially inward (the fourth boss is obscured in the figures). The base 704 includes first) and second stop members 736, 738 that each extend radially outward and are configured to interact with the first, second, third, and fourth bosses 724, 726, 728. The first and second stop members 736, 738 are on opposed to one another about 180° apart from one another around a circumference of the base 704. The first and second stop members 736, 738 are configured to stop rotation of the collar 718 relative to the base 704. A position of the collar 718 relative to the base 704 affects a position of the first and second pawls 706, 708 relative to the base 704, and thus whether or not the first and second pawls 706, 708 are in positions to lock to the adapter 600, as discussed further below.

Figure 14:
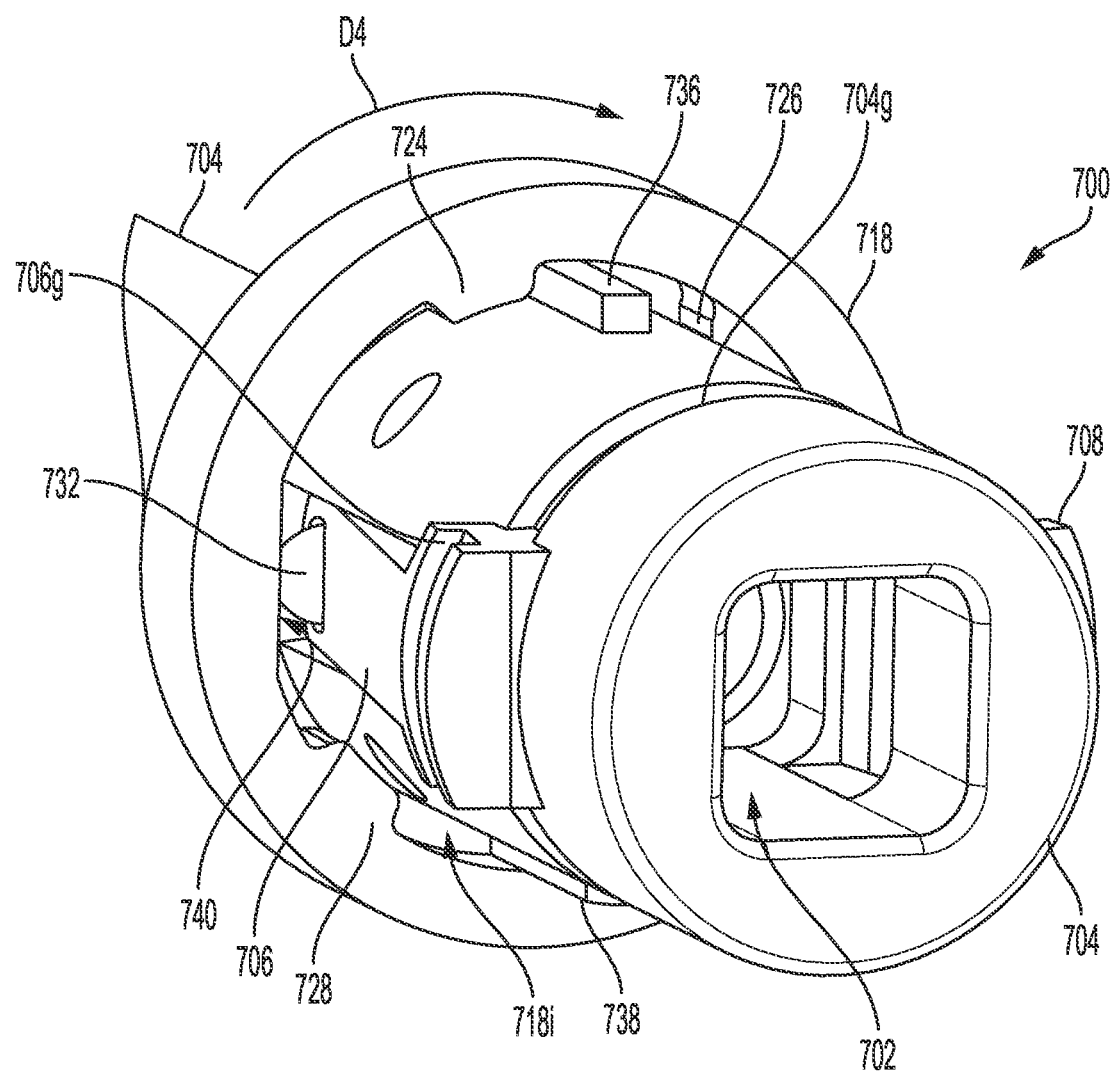
FIG. 14 is a perspective view of another embodiment of a locking assembly.
Figure 15:
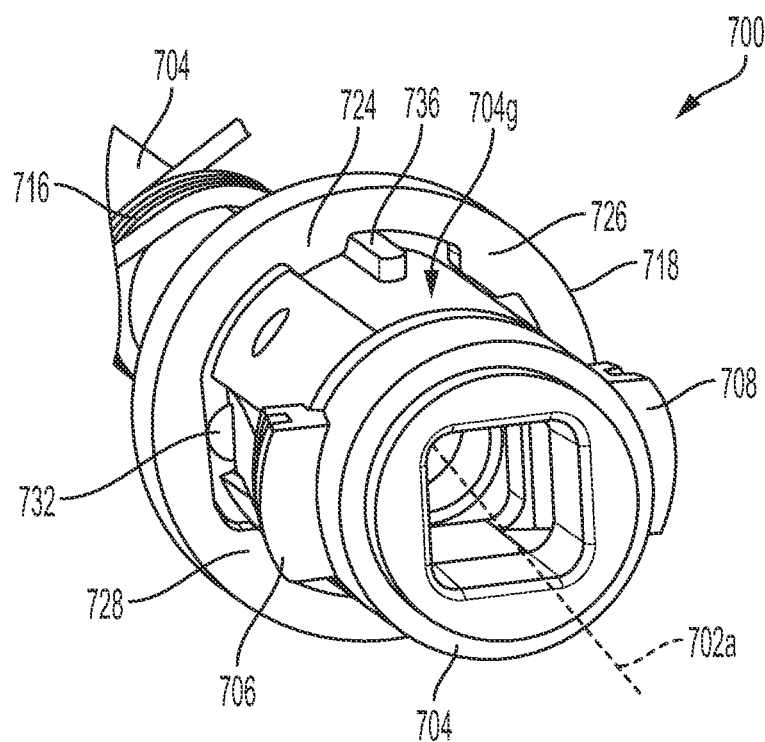
FIG. 15 is another perspective view of the locking assembly of FIG. 14.

The first stop member 736 is configured to interact with the first boss 724 and the second boss 726 positioned on either side of the first stop member 736, and the second stop member 738 is configured to interact with the third boss 728 and the fourth boss positioned on either side of the second stop member 738. The second boss 726 is configured to abut a first side of the first stop member 736 and the third boss 728 is configured abut a first side of the second stop member 738 simultaneously with the second boss 726 abutting the first side of the first stop member 736 to stop rotation of the collar 718 in the first direction D3, as shown in FIG. 19. The collar 718 in this position with the second boss 726 abutting the first stop member 736 and the third boss 728 abutting the second stop member 738 corresponds to the locking assembly 700 being in the locked configuration. The first boss 724 is configured to abut a second, opposite side of the first stop member 736 and the fourth boss is configured abut a second side of the second stop member 738 simultaneously with the first boss 724 abutting the second side of the first stop member 736 to stop rotation of the collar 718 in a second direction D4, as shown in FIG. 14, that is opposite to the first direction D3. The collar 718 in this position corresponds to the locking assembly 700 being in the unlocked configuration.

The collar 718 includes a first cam ramp 740 and a second cam ramp (obscured in the figures) configured to operatively engage the first and second cam followers 732, 734, respectively. The first cam ramp 740 extends along an inner surface of the collar 718, and the second cam ramp extends along the inner surface of the collar 718 opposite to the first cam ramp 740. The first cam ramp 740 and the second cam ramp are configured to operative engage the first and second cam followers 732, 734, respectively, to facilitate pivoting of the first and second pawls 706, 708 at their respective pivot points 710, 712. With the locking assembly 700 in the unlocked configuration, the first cam ramp 740 is engaged with the first cam follower 732, which presses the first cam follower 732 radially inward into the cavity 706c of the first pawl 706 to urge the first pawl 706 to be pivoted radially outward, and the second cam ramp is engaged with the second cam follower 734, which presses the second cam follower 734 radially inward into the cavity 708c of the second pawl 708 to urge the second pawl 708 to be pivoted radially outward. With the locking assembly 700 in the locked configuration, the first cam ramp 740 is not engaged with the first cam follower 732, so the first cam follower 732 is not being pressed radially inward into the cavity 706c of the first pawl 706 such that the first pawl 706 is not pivoted radially outward, and the second cam ramp is not engaged with the second cam follower 734, so the second cam follower 734 is not being pressed radially inward into the cavity 708c of the second pawl 708 such that the second pawl 708 is not pivoted radially outward.

The locking assembly 700 is configured to automatically move to the locked configuration in response to the locking assembly's engagement with the adapter 600. In an exemplary embodiment, the adapter 600 being moved into the cavity 702 along the longitudinal axis 702A defined by the cavity 702 is configured to cause the locking assembly 700 to automatically move to the locked configuration. The adapter 600 can be moved into the cavity 702 by moving the adapter 600 in a rearward direction relative to the locking assembly 700, by moving the locking assembly 700 forward relative to the adapter 600, or by both moving the adapter 600 in a rearward direction relative to the locking assembly 700 and moving the locking assembly 700 forward relative to the adapter 600.

Figure 17:
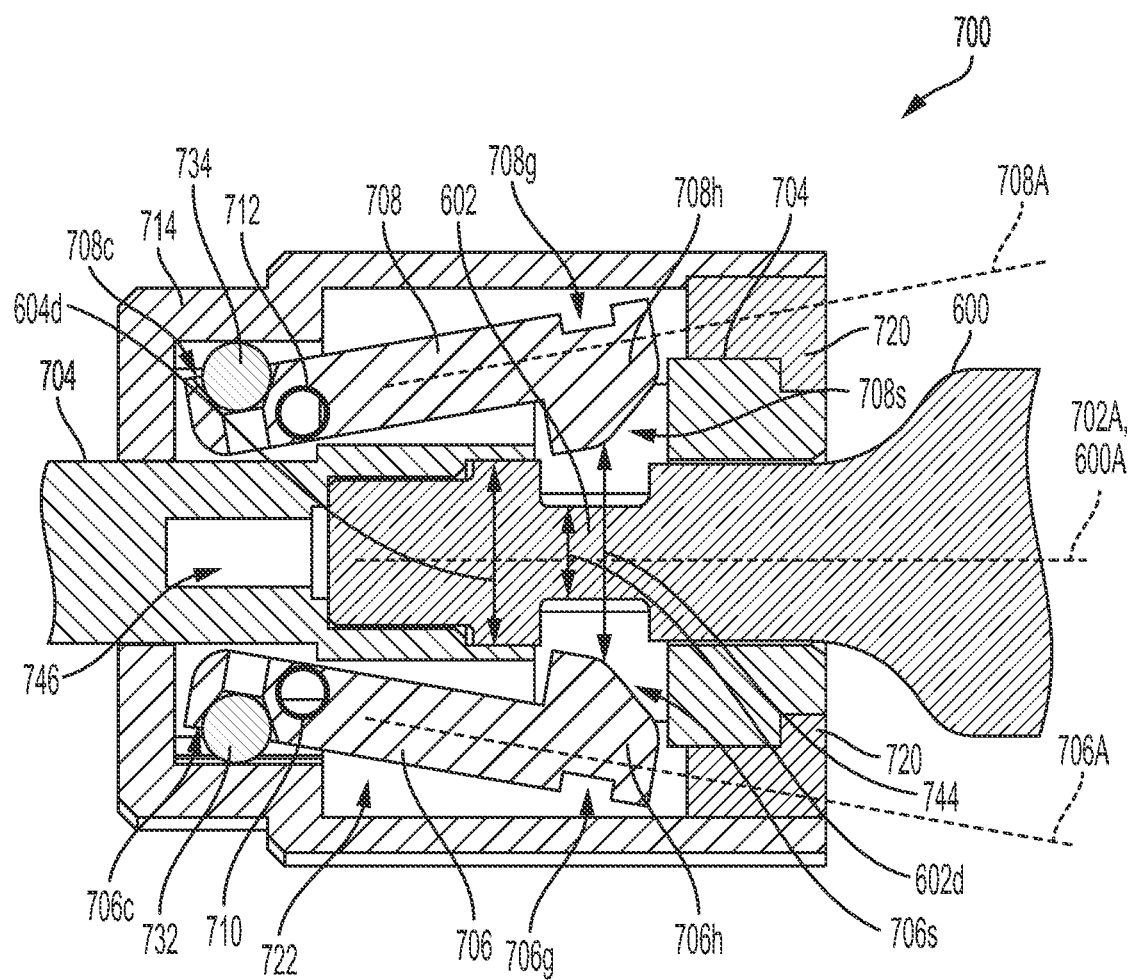
FIG. 17 is a side cross-sectional view of the locking assembly of FIG. 14 with the adapter of FIG. 13 in a cavity of the locking assembly.

As shown in FIGS. 17 and 20, a head 706h of the first pawl 706 is located forwardly, a head 708h of the second pawl 708 is located forwardly, the first pivot point 710 for the first pawl 706 is located rearwardly, and the second pivot point 712 for the second pawl 708 is located rearwardly. The heads 706h, 708h of the first and second pawls 706, 708 each include a sloped surface 706s, 708s that slopes radially inward in a rearward direction. The sloped pawl surfaces 706s, 708s face one another. A gap 744 is defined between the sloped pawl surfaces 706s, 708s. With the locking assembly 700 in the locked configuration, a minimum width of the gap 744 is less than a width of the cavity 702 rearward of the pawls 706, 708 and is less than the width of the rearward portion of the adapter 600 that is being inserted into the cavity 702.

With the locking assembly 700 in its default, locked configuration, the adapter 600 moving into the cavity 702, before being seated and locked therein, encounters the sloped pawl surfaces 706s, 708s of the first and second pawls 706, 708. The adapter 600 being moved longitudinally into the cavity 702 causes the adapter 600 to engage the first and second sloped pawl surfaces 706s, 708s. Because the adapter 600 is wider than the gap 744 with the locking assembly 700 in the locked configuration, and because the first and second pawls 706, 708 are movably attached to the base 704 having the cavity 702 formed therein, the adapter 600 can move rearwardly through the gap 744 by slidingly engaging the sloped pawl surfaces 706s, 708s, which causes the first and second pawls 706, 708 to pivot at their respective pivot points 710, 712 and thereby widen the gap 744. The adapter 600 can thus be moved longitudinally into the cavity 702 until the rearward facing surface of the adapter 600 abuts a forward facing surface of the base 604 that defines a rearward end of the cavity 702.

As discussed above, the reduced diameter portion 602 of the adapter 600 has a smaller diameter 602d than the diameter 604d of the portion 604 of the adapter 600 rearward of the reduced diameter portion 602 and than the diameter 606d of the portion 606 of the adapter 600 forward of the reduced diameter portion 602. The diameter 604d of the portion 604 of the adapter 600 rearward of the reduced diameter portion 602 is moved rearwardly past the sloped pawl surfaces 706s, 708s and the first and second pawl heads 706h, 708h. When the reduced diameter portion 602 of the adapter 600 becomes axially aligned with the first and second pawl heads 706h, 708h, the first and second pawls 706, 708 are no longer being urged outwardly by the adapter 600 and are allowed to freely pivot inwardly toward their initial, default position, as urged by the first biasing element 730. The first and second pawls 706, 708 will thus become seated in the reduced diameter portion 602, as shown in FIG. 20. The first and second pawls 706, 708 being seated in the reduced diameter portion 602 of the adapter 600 prevents the adapter 600 from moving longitudinally relative to the locking assembly 700 (and thus relative to the surgical impacting tool that includes the locking assembly 700).

As mentioned above, the locking assembly 700 is configured to move from the locked configuration to the unlocked configuration. In an exemplary embodiment, the housing 714 of the locking assembly 700 being rotated about the longitudinal axis 702A defined by the cavity 702 (and thus about the adapter's longitudinal axis 600A coaxial therewith) relative to the adapter 600 and to the base 704 is configured to cause the locking assembly 700 to move from the locked configuration to the unlocked configuration to allow the adapter 600 to then be moved longitudinally along the longitudinal axis 702A defined by the cavity 702 (and thus about the adapter's longitudinal axis 600A coaxial therewith). The adapter 600 can be moved out of the cavity 702 by moving the adapter 600 in a forward direction relative to the locking assembly 700, by moving the locking assembly 700 rearward relative to the adapter 600, or by both moving the adapter 600 in a forward direction relative to the locking assembly 700 and moving the locking assembly 700 rearward relative to the adapter 600.

With the locking assembly 700 in the locked position so as to be releasably attached to the adapter 600, the housing 714 is rotated in the second direction D4, as shown in FIG. 14, that is opposite to the first direction D3 in which the housing 714 is biased. The rotation of the housing 714 in the second direction D4 also causes the collar 718 fixedly attached thereto to rotate in the second direction D4, which is clockwise in this illustrated embodiment. The rotation of the collar 718 causes the first, second, third, and fourth bosses 724, 726, 728 of the collar 718 to rotate. The rotation of the first, second, third, and fourth bosses 724, 726, 728 in the second direction D4 causes the second boss 726 to move out of abutting contact with the first stop member 736, causes the third boss 728 to move out of abutting contact with the second stop member 738, causes the first cam follower 732 to begin sliding along the first cam ramp 740 to begin pushing the first cam follower 732 into the first pawl's cavity 706c, and causes the second cam follower 734 to begin sliding along the second cam ramp to begin pushing the second cam follower 734 into the second pawl's cavity 708c. The first and second pawls 706, 708 thus begin to pivot at their respective pivot points 710, 712. Continued rotation of the collar 718 in the second direction D4 causes the first boss 724 to abut the first stop member 736, causes the fourth boss to abut the second stop member 738, continues the sliding of the first cam follower 732 along the first cam ramp 740 to push the first cam follower 732 into the first pawl's cavity 706c, and continues the sliding of the second cam follower 734 along the second cam ramp to push the second cam follower 734 into the second pawl's cavity 708c, as shown in FIG. 14. The first boss 724 abutting the first stop member 736 and the fourth boss abutting the second stop member 738 stops the collar 718 from rotating and thus stops the pivoting of the first and second pawls 706, 708 by stopping the first and second cam followers 732, 734 from being pushed into their respective cavities 706c, 708c. The gap 744 between the first and second pawls 706, 708 has thus increased, as shown in FIG. 17. The widened gap 744 allows for the adapter 600 to be moved longitudinally out of the cavity 702 since the diameter 604d of the adapter's portion 604 rearward of the reduced diameter portion 602 can now pass through the gap 744.

After the adapter 600 has been removed from the cavity 702, the housing 714 can be released, thereby allowing the housing 714 and the collar 718 to rotate in the first direction D3 under force of the biasing element 716 to return the locking assembly 700 to its initial configuration. The housing 714 can be manually moved in the first direction D3 to help the housing's and collar's rotational movement, or the housing 714 and the collar 718 can be allowed to move in the first direction D3 fully under force provided by the biasing element 716.

Figure 16:
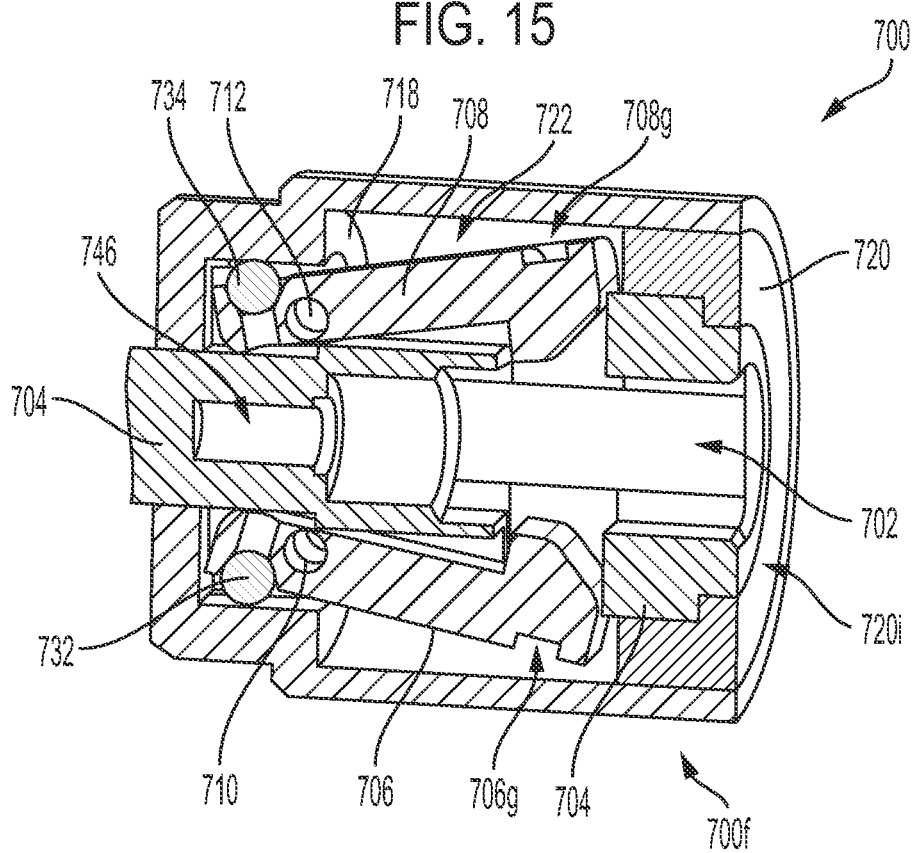
FIG. 16 is a perspective, cross-sectional view of the locking assembly of FIG. 14.

As shown in FIGS. 16, 17, and 20, the base 704 includes a blind hole 746 rearward of and in communication with the cavity 702. A third biasing element (not shown) can be disposed in the blind hold 746 similar to that discussed above regarding the blind hole 532 of FIG. 13. The locking assembly 700 can omit the blind hole 746 if a third biasing element is not present.

The present disclosure has been described above by way of example only within the context of the overall disclosure provided herein. It will be appreciated that modifications within the spirit and scope of the claims may be made without departing from the overall scope of the present disclosure.

What is claimed is:

1. A surgical tool, comprising:
an adapter;
a surgical implement configured to impact bone, the surgical implement being a broach or a chisel, and the surgical implement either being non-releasably attached to the adapter or being configured to releasably attach to the adapter; and
a locking assembly configured to releasably attach to the adapter, wherein:
the locking assembly has a locked configuration in which the locking assembly is releasably attached to the adapter;
the locking assembly has an unlocked configuration in which the locking assembly is not releasably attached to the adapter;
the locking assembly includes a cavity configured to, in the locked configuration, seat a portion of the adapter therein;
a direction of the impacting is, with the locking assembly releasably attached to the adapter and with the surgical implement either non-releasably attached to the adapter or releasably attached to the adapter, substantially along a longitudinal axis defined by the cavity;
the longitudinal axis defined by the cavity is, with the locking assembly releasably attached to the adapter, coaxial with a longitudinal axis of the adapter;
the locking assembly is configured to move from the unlocked configuration to the locked configuration in response to the adapter being moved into the cavity substantially along a longitudinal axis defined by the cavity; and
the locking assembly is configured to move from the locked configuration to the unlocked configuration in response to a housing of the locking assembly being rotated about the longitudinal axis and then the adapter being moved out of the cavity substantially along the longitudinal axis.

2. The tool of claim 1, wherein the locking assembly comprises a first pawl defining a first longitudinal axis that is substantially perpendicular to the longitudinal axis defined by the cavity with the locking assembly in the unlocked configuration, and a second pawl defining a second longitudinal axis that is substantially perpendicular to the longitudinal axis defined by the cavity with the locking assembly in the unlocked configuration.

3. The tool of claim 1, wherein the locking assembly comprises a base having the cavity formed therein, a first pawl pivotally coupled to the base at a first pivot point, and a second pawl pivotally coupled to the base at a second pivot point.

4. The tool of claim 3, wherein the locking assembly being configured to move from the unlocked configuration to the locked configuration comprises
the adapter being moved into the cavity substantially along the longitudinal axis and thereby causing the first pawl to pivot at the first pivot point and the second pawl to pivot at the second pivot point.

5. The tool of claim 4, wherein the locking assembly being configured to move from the locked configuration to the unlocked configuration comprises
the housing being rotated about the longitudinal axis and thereby causing the housing to rotate relative to the base, and
thereafter the adapter being moved out of the cavity substantially along the longitudinal axis and thereby causing the first pawl to pivot at the first pivot point and the second pawl to pivot at the second pivot point.

6. The tool of claim 4, wherein the locking assembly being configured to move from the locked configuration to the unlocked configuration comprises the housing being rotated about the longitudinal axis and thereby causing the housing to rotate relative to the base, causing the first pawl to pivot at the first pivot point, and causing the second pawl to pivot at the second pivot point, and thereafter the adapter being moved out of the cavity substantially along the longitudinal axis.

7. The tool of claim 3, wherein the locking assembly comprises a biasing element that biases the housing to a position corresponding to the unlocked configuration of the locking assembly.

8. The tool of claim 3, wherein the locking assembly comprises a first biasing element that biases the housing to a position corresponding to the locked configuration of the locking assembly; and the locking assembly comprises a second biasing element that biases the first and second pawls to positions corresponding to the locked configuration of the locking assembly.

9. The tool of claim 1, wherein the locking assembly comprises a first pawl defining a first longitudinal axis that is substantially parallel to the longitudinal axis defined by the cavity with the locking assembly in the locked configuration, and a second pawl defining a second longitudinal axis that is substantially parallel to the longitudinal axis defined by the cavity with the locking assembly in the locked configuration.

10. The tool of claim 1, wherein the locking assembly is configured to automatically move from the unlocked configuration to the locked configuration without the adapter being rotated.

11. The tool of claim 1, wherein the locking assembly is configured to, in the locked configuration, seat the adapter in the cavity at each of a plurality of predetermined angular orientations relative to the locking assembly.

12. The tool of claim 11, wherein the plurality of predetermined angular orientations are each about 90 degrees apart from one another.

13. The tool of claim 1, wherein the surgical implement conforms to a shape of a stem of a prosthetic device.

14. The tool of claim 1, wherein a surgical impacting tool includes the locking assembly; and with the surgical implement operably coupled to the locking assembly, the surgical impacting tool is configured to drive the impacting of the surgical implement.

15. The tool of claim 2, wherein, in response to the adapter being moved into the cavity substantially along the longitudinal axis defined by the cavity, the first pawl is configured to pivot at a first pivot point and the second pawl is configured to pivot at a second pivot point.

16. The tool of claim 2, wherein the adapter being moved into the cavity substantially along the longitudinal axis defined by the cavity is configured to cause the first pawl to pivot at a first pivot point from a first default configuration and then back toward the first default configuration;

the adapter being moved into the cavity substantially along the longitudinal axis defined by the cavity is configured to cause the second pawl to pivot at a second pivot point from a second default configuration and then back toward the second default configuration; and the housing of the locking assembly being rotated about the longitudinal axis is configured to cause the first pawl to pivot at the first pivot point and the second pawl to pivot at the second pivot point.

17. The tool of claim 3, wherein, in response to the adapter being moved into the cavity substantially along the longitudinal axis defined by the cavity, the first pawl is configured to pivot at the first pivot point and the second pawl is configured to pivot at the second pivot point.

18. The tool of claim 3, wherein the adapter being moved into the cavity substantially along the longitudinal axis defined by the cavity is configured to cause the first pawl to pivot at the first pivot point from a first default configuration and then back toward the first default configuration;

the adapter being moved into the cavity substantially along the longitudinal axis defined by the cavity is configured to cause the second pawl to pivot at the second pivot point from a second default configuration and then back toward the second default configuration; and the housing of the locking assembly being rotated about the longitudinal axis is configured to cause the first pawl to pivot at the first pivot point and the second pawl to pivot at the second pivot point.

19. The tool of claim 1, wherein an orthopedic impacting tool includes the locking assembly; and with the surgical implement operably coupled to the locking assembly, the orthopedic impacting tool is configured to drive the impacting of the surgical implement.

20. A surgical tool, comprising:

an adapter configured to releasably attach to a surgical implement configured to impact bone; and an orthopedic impacting tool including a locking assembly configured to releasably attach to the adapter, wherein:

the locking assembly has a locked configuration in which the locking assembly is releasably attached to the adapter;

the locking assembly has an unlocked configuration in which the locking assembly is not releasably attached to the adapter;

the locking assembly includes a cavity configured to, in the locked configuration, seat a portion of the adapter therein;

the locking assembly is configured to move from the unlocked configuration to the locked configuration in response to the adapter being moved into the cavity substantially along a longitudinal axis defined by the cavity; and the locking assembly is configured to move from the locked configuration to the unlocked configuration in response to a housing of the locking assembly being rotated about the longitudinal axis and then the adapter being moved out of the cavity substantially along the longitudinal axis.

* * * * *